(12) United States Patent
Barth et al.

(10) Patent No.: US 7,524,971 B2
(45) Date of Patent: Apr. 28, 2009

(54) 1,5-DIARYLPYRROLE DERIVATIVES, PREPARATION METHOD THEREOF AND APPLICATION OF SAME IN THERAPEUTICS

(75) Inventors: Francis Barth, Saint Georges d'Orques (FR); Christian Congy, Saint Gely du Fesc (FR); Laurent Hortala, Jacou (FR); Murielle Rinaldi-Carmona, Saint Georges d'Orques (FR)

(73) Assignee: Sanofi - Aventis, Paris (FR)

( * ) Notice: Subject to any disclaimer, the term of this patent is extended or adjusted under 35 U.S.C. 154(b) by 0 days.

(21) Appl. No.: 11/832,851

(22) Filed: Aug. 2, 2007

(65) Prior Publication Data
US 2008/0015245 A1    Jan. 17, 2008

Related U.S. Application Data

(63) Continuation of application No. PCT/FR2006/000356, filed on Feb. 16, 2006.

(30) Foreign Application Priority Data
Feb. 17, 2005   (FR) .................................. 05 01660

(51) Int. Cl.
*C07D 207/30* (2006.01)
(52) U.S. Cl. .................................................. 548/563
(58) Field of Classification Search ................. 548/563
See application file for complete search history.

(56) References Cited

U.S. PATENT DOCUMENTS 5,624,941 A    4/1997    Barth et al.

FOREIGN PATENT DOCUMENTS

WO    WO 2004/058249    7/2004

OTHER PUBLICATIONS

Cerreto, F., et al., Studies on Anti-Candida Agents With A Pyrrole Moeity. Synthesis and Microbiological Activity of Some 3-Aminomethyl-1,5-Diaryl-2-Methyl-Pyrrole Derivatives, Eur J Med Chem (1992) vol. 27, pp. 701-708.

*Primary Examiner*—Rebecca L Anderson
*Assistant Examiner*—Robert Havlin
(74) *Attorney, Agent, or Firm*—Balaram Gupta

(57) ABSTRACT

The invention relates to compounds having formula (I):

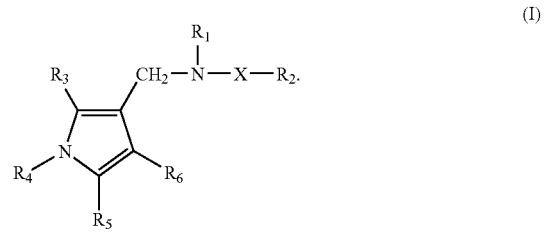

Wherein X, $R_1$, $R_2$, $R_3$, $R_4$, $R_5$ and $R_6$ are as defined herein. The invention also relates to a method of preparing said compounds and to die application thereof in therapeutics.

9 Claims, No Drawings

1,5-DIARYLPYRROLE DERIVATIVES, PREPARATION METHOD THEREOF AND APPLICATION OF SAME IN THERAPEUTICS

This application is a continuation of International application No. PCT/FR2006/000,356, filed Feb. 16, 2006, which is incorporated herein by reference in its entirety; which claims the benefit of priority of French Patent Application No. 05/01, 660, filed Feb. 17, 2005.

The present invention relates to 1,5-diarylpyrrole derivatives, to the preparation thereof and to the therapeutic use thereof.

Diphenylpyrazole derivatives with affinity for the cannabinoid $CB_1$, receptors have been described especially in U.S. Pat. No. 5,624,941, EP 0 576 357, EP 0 656 354 and EP 1 150 961.

Patent application WO 2005/058 249 describes diarylpyrrole derivatives as cannabinoid receptor modulators and patent application WO 2003/027 069 describes diarylpyrrole derivatives that are active towards obesity.

Novel 1,5-diaryl-3-aminomethylpyrrole derivatives that have antagonistic properties on the cannabinoid $CB_1$ receptors have now been found.

One subject of the present invention is compounds corresponding to the formula:

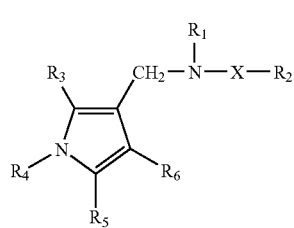

(I)

in which:
X represents a group

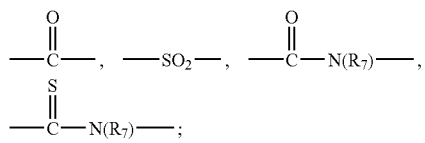

$R_1$ represents a hydrogen atom or a $(C_1\text{-}C_3)$alkyl group;
$R_2$ represents:
- a $(C_1\text{-}C_{12})$alkyl, which is unsubstituted or substituted with one or more substituents independently chosen from a hydroxyl, a $(C_1\text{-}C_4)$alkoxy, a trifluoromethyl radical and a trifluoromethoxy radical;
- a $(C_3\text{-}C_{12})$ non-aromatic carbocyclic radical, which is unsubstituted or substituted one or more times with a $(C_1\text{-}C_3)$alkyl or a $(C_1\text{-}C_3)$alkoxy;
- a $(C_3\text{-}C_7)$cycloalkylmethyl, which is unsubstituted or substituted one or more times on the carbocycle with a $(C_1\text{-}C_3)$alkyl or a $(C_1\text{-}C_3)$alkoxy;
- a phenyl, which is unsubstituted or substituted one or more times with substituents independently chosen from a halogen atom, a $(C_1\text{-}C_4)$alkyl, a $(C_1\text{-}C_4)$alkoxy, a cyano, a trifluoromethyl radical, a trifluoromethoxy radical, a trifluoromethoxy radical, a di$(C_1\text{-}C_4)$alkylamino radical, a group $S(O)_m$Alk, a $(C_1\text{-}C_4)$alkylcarbonyl group, or from a phenyl, 1-pyrrolyl, imidazolyl, pyridyl or pyrazolyl radical, the said radicals being unsubstituted or substituted one or more times with a $(C_1\text{-}C_4)$alkyl;
- a benzodioxolyl, a dihydrobenzofuryl or a dihydrobenzodioxinyl;
- a methyl substituted with a benzodioxolyl, a dihydrobenzofuryl or a dihydrobenzodioxinyl;
- a 1,2,3,4-tetrahydronaphthalenyl, which is unsubstituted or substituted one or more times with a $(C_1\text{-}C_4)$ alkyl;
- a benzyl, which is unsubstituted or substituted on the phenyl one or more times with substituents independently chosen from a halogen atom, a $(C_1\text{-}C_4)$alkyl, a $(C_1\text{-}C_4)$alkoxy and a trifluoromethyl or trifluoromethoxy radical, and alpha-unsubstituted or alpha-substituted with a pyrrolyl or phenoxy radical;
- a benzhydryl or a benzhydrylmethyl;
- a phenethyl, which is unsubstituted or substituted on the phenyl with a halogen, a $(C_1\text{-}C_4)$alkyl or a trifluoromethyl radical;
- an aromatic heterocyclic radical chosen from thienyl, furyl, pyrrolyl, pyridyl, pyrazolyl, oxazolyl and imidazolyl, the said radical being unsubstituted or substituted with one or more substituents independently chosen from a halogen atom, a $(C_1\text{-}C_4)$alkyl, a $(C_1\text{-}C_4)$alkoxy, a trifluoromethyl radical and a trifluoromethoxy radical;
- a methyl substituted with a heterocyclic radical independently chosen from thienyl, furyl, pyrrolyl, pyridyl, pyrazolyl, oxazolyl and imidazolyl, the said radical being unsubstituted or substituted with one or more substituents independently chosen from a halogen atom, a $(C_1\text{-}C_4)$alkyl, a $(C_1\text{-}C_4)$alkoxy and a trifluoromethyl radical;
- an indolyl, which is unsubstituted or substituted one or more times with substituents independently chosen from a halogen atom, a $(C_1\text{-}C_4)$alkyl, a $(C_1\text{-}C_4)$ alkoxy, a trifluoromethyl radical, a trifluoromethoxy radical, a group $S(O)_m$Alk, a $(C_1\text{-}C_4)$alkylcarbonyl group and a phenyl;
- a benzothiazolyl, which is unsubstituted or substituted one or more times with substituents independently chosen from a halogen atom, a $(C_1\text{-}C_4)$alkyl, a $(C_1\text{-}C_4)$alkoxy, a trifluoromethyl radical a trifluoromethoxy radical, a group $S(O)_m$Alk, a $(C_1\text{-}C_4)$alkylcarbonyl group and a phenyl;
- a methyl substituted with one or two $(C_1\text{-}C_4)$alkyl and with a phenoxy or 1-pyrrolyl radical, the said radical being unsubstituted or substituted with a halogen, a $(C_1\text{-}C_4)$alkyl or a trifluoromethyl;

$R_3$ represents a $(C_1\text{-}C_5)$alkyl or a $(C_3\text{-}C_7)$cycloalkyl;
$R_4$ represents a phenyl, which is unsubstituted or substituted one or more times with substituents independently chosen from a halogen atom, a $(C_1\text{-}C_4)$alkyl, a $(C_1\text{-}C_4)$ alkoxy, a trifluoromethyl radical or a group $S(O)_m$Alk;
$R_5$ represents a phenyl, which is unsubstituted or substituted one or more times with substituents independently chosen from a halogen atom, a $(C_1\text{-}C_4)$alkyl, a $(C_1\text{-}C_4)$ alkoxy, a trifluoromethyl radical or a group $S(O)_m$Alk;
$R_6$ represents a hydrogen atom or a $(C_1\text{-}C_5)$alkyl group;
$R_7$ represents a hydrogen atom or a $(C_1\text{-}C_3)$alkyl;
m represents 0, 1 or 2;
Alk represents a $(C_1\text{-}C_4)$alkyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of hydrates or solvates, i.e. in the form of associations or combinations with one or more water molecules or with a solvent. Such hydrates and solvates also form part of the invention.

Among the compounds of formula (I) that are the subject of the invention, the compounds of formula (I) are distinguished, in which:

X represents a group

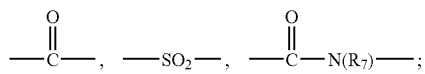

$R_1$ represents a hydrogen atom or a $(C_1-C_3)$alkyl group;
$R_2$ represents:
  a $(C_1-C_7)$alkyl;
  a $(C_3-C_{17})$cycloalkyl, which is unsubstituted or substituted one or more times with a $(C_1-C_3)$alkyl group;
  a $(C_3-C_7)$cycloalkylmethyl, which is unsubstituted or substituted one or more times on the carbocycle with a $(C_1-C_3)$alkyl;
  a phenyl, which is unsubstituted or substituted one or more times with substituents independently chosen from a halogen atom, a $(C_1-C_4)$alkyl, a $(C_1-C_4)$alkoxy, a cyano, a trifluoromethyl, a trifluoromethoxy radical, a group $S(O)_m$Alk, a $(C_1-C_4)$alkylcarbonyl group and a phenyl;
  a benzyl, which is unsubstituted or substituted one or more times with substituents independently chosen from a halogen atom, a $(C_1-C_4)$alkyl, a $(C_1-C_4)$alkoxy and a trifluoromethyl radical;
  an indolyl, which is unsubstituted or substituted one or more times with substituents independently chosen from a halogen atom, a $(C_1-C_4)$alkyl, a $(C_1-C_4)$alkoxy, a trifluoromethyl radical, a trifluoromethoxy radical, a group $S(O)_m$Alk, a $(C_1-C_4)$alkylcarbonyl group and a phenyl;
$R_3$ represents a $(C_1-C_5)$alkyl or a $(C_3-C_7)$cycloalkyl;
$R_4$ represents a phenyl, which is unsubstituted or substituted one or more times with substituents independently chosen from a halogen atom, a $(C_1-C_4)$alkyl, a $(C_1-C_4)$alkoxy, a trifluoromethyl radical and a group $S(O)_m$Alk;
$R_5$ represents a phenyl, which is unsubstituted or substituted one or more times with substituents independently chosen from a halogen atom, a $(C_1-C_4)$alkyl, a $(C_1-C_4)$alkoxy, a trifluoromethyl radical and a group $S(O)_m$Alk;
$R_6$ represents a hydrogen atom or a $(C_1-C_5)$alkyl group;
$R_7$ represents a hydrogen atom or a $(C_1-C_3)$alkyl;
m represents 0, 1 or 2;
Alk represents a $(C_1-C_4)$alkyl.

The term "halogen atom" means a bromine, chlorine, fluorine or iodine atom.

The terms "$(C_1-C_3)$alkyl", "$(C_1-C_4)$alkyl", "$(C_1-C_5)$alkyl", "$(C_1-C_7)$alkyl" and "$(C_1-C_{12})$alkyl", respectively, mean a linear or branched alkyl radical of one to three carbon atoms, of one to four carbon atoms, of one to five carbon atoms, of one to seven carbon atoms or of one to twelve carbon atoms, respectively, for instance a methyl, ethyl, propyl, isopropyl, butyl, isobutyl, sec-butyl, tert-butyl, pentyl, isopentyl, hexyl, isohexyl, heptyl, 2-propylbutyl, octyl, nonyl, decyl, undecyl or dodecyl radical.

The term "$(C_1-C_4)$alkoxy" means a linear or branched alkoxy radical of one to four carbon atoms, such as a methoxy, ethoxy, propoxy, isopropoxy, butoxy, sec-butoxy or tert-butoxy radical.

The term "$(C_3-C_7)$cycloalkyl" means a cyclic alkyl group of 3 to 7 carbon atoms, such as a cyclopropyl, cyclobutyl, cyclopentyl, cyclohexyl or cycloheptyl group.

The term "$C_3-C_{12}$ non-aromatic carbocyclic radical" means: a monocyclic radical or a fused or bridged bicyclic or tricyclic radical; die term "monocyclic radical" means a cycloalkyl, for example cyclopropyl, cyclobutyl, cyclopentyl, cyclohexyl, or cycloheptyl, the cyclopentyl, cyclohexyl and cycloheptyl radicals being preferred; the term "fused or bridged bicyclic or tricyclic radical" means, for example, bicyclo[2.2.1]heptyl, bicyclo[2.2.2]octyl, bicyclo[3.2.1]octyl or adamantyl.

Among the compounds of formula (I) that are subjects of the invention, the following are distinguished:
  the compounds of formula (IA) in which —X— represents a —CO— radical and the substituents $R_1$ to $R_6$ are as defined for the compounds of formula (I);
  the compounds of formula (IB) in which —X— represents an $SO_2$— radical and the substituents $R_1$ to $R_6$ are as defined for the compounds of formula (I);
  the compounds of formula (IC) in which —X— represents a radical CON($R_7$)— and the substituents $R_1$ to $R_7$ are as defined from the compounds of formula (I);
  the compounds of formula (ID) in which —X— represents a radical —CSN($R_7$)— and the substituents $R_1$ to $R_7$ are as defined for the compounds of formula (I).

Among the compounds that are subjects of the invention, the preferred compounds are those of formula (I) in which:
  $R_1$ represents a hydrogen atom;
  and/or $R_3$ represents a methyl;
  and/or $R_4$ and $R_5$ represent, independently of each other, a 2,4-dichlorophenyl and a 4-chlorophenyl or a 2,4-dichlorophenyl and a 4-bromophenyl or a 2,4-dichlorophenyl and a 4-methoxyphenyl;
  and/or $R_6$ represents a hydrogen atom;
  $R_2$ and X have one of the values defined for (I);
  and/or $R_7$ represents a hydrogen atom;

and also the hydrates or solvates thereof.

The compounds that are most particularly preferred are those of formula (I) in which:
  X is as defined for (I);
  $R_1$ represents a hydrogen atom;
  $R_3$ represent a methyl;
  $R_4$ and $R_5$ represent, independently of each other, a 2,4-dichlorophenyl and a 4-chlorophenyl or a 2,4-dichlorophenyl and a 4-bromophenyl or a 2,4-dichlorophenyl and a 4-methoxyphenyl;
  $R_6$ and $R_7$ represent a hydrogen atom;
  $R_2$ represents:
  a phenethyl;
  a tetrahydronaphthyl;
  a benzyl, which is unsubstituted or substituted one or more times with substituents independently chosen from a halogen atom, a trifluoromethyl, a methoxy or a cyano;
  a phenyl, which is unsubstituted or substituted one or more times with substituents independently chosen from a halogen atom, a trifluoromethyl, a methoxy, a cyano and a phenyl;
  a branched $C_3-C_8$ alkyl;
  a $C_6-C_7$ cycloalkyl, which is unsubstituted or substituted with a methyl;

a hydroxy ($C_1$-$C_4$)alkyl, which is unsubstituted or substituted with one or more fluorine atoms;

a 2-indolyl;

a heterocyclic radical chosen from pyrazolyl and furyl, the said radical being unsubstituted or substituted with one or more substituents independently chosen from a ($C_1$-$C_4$)alkyl and a trifluoromethyl;

a methyl substituted with a ($C_1$-$C_4$)alkyl and with a pyrrolyl;

a methyl substituted with a phenyl and with a pyrrolyl.

More particularly, the preferred compounds are those of formula (I) in which:

$R_1$ represents a hydrogen atom;

$R_3$ represents a methyl;

$R_4$ represents a 4-methoxyphenyl, a 4-chlorophenyl, a 4-methoxyphenyl or a 2,4-dichlorophenyl;

$R_5$ represents a 4-chlorophenyl, a 4-methoxyphenyl or a 2,4-dichlorophenyl;

$R_6$ represents a hydrogen atom;

X represents a —CO—, —$SO_2$—, —CONH— or —CSNH— group;

$R_2$ represents a group chosen from a chlorophenyl, a trifluoromethylphenyl, a methoxyphenyl, a cyanophenyl, a 2-phenylphenyl, a trifluoromethylbenzyl, a 4-heptyl, a cycloheptyl, a 3,3,3-trifluoro-2-hydroxy-2-methylpropyl, a 2,2-dimethyl-1(1H-pyrrol-1-yl)propyl, a 2-indolyl, a 5-methyl-2-trifluoromethyl-3-furyl, a 1-ethyl-3-tert-butyl-5-pyrrolyl, a phenethyl, a 1,2,3,4-tetrahydro-2-naphthyl and a 1,2,3,4-tetrahydro-1-naphthyl;

and also the hydrates or solvates thereof.

The following compounds are most particularly preferred:

N-{[5-(2,4-dichlorophenyl)-1-(4-methoxyphenyl)-2-methyl-1H-pyrrol-3-yl]methyl}-5-methyl-2-(trifluoromethyl)furan-3-sulfonamide;

N-{[1-(4-chlorophenyl)-5-(2,4-dichlorophenyl)-2-methyl-1H-pyrrol-3-yl]methyl}-3-cyanobenzenesulfonamide;

N-{[1-(4-chlorophenyl)-5-(2,4-dichlorophenyl)-2-methyl-1H-pyrrol-3-yl]methyl}-3-methoxybenzenesulfonamide;

In accordance with the invention, the compounds of formula (I) may be prepared according to a process that is characterized in that:

a compound of formula:

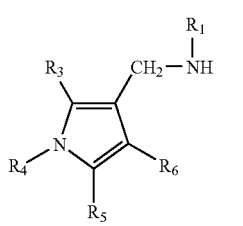

(II)

in which $R_1$, $R_3$, $R_4$, $R_5$ and $R_6$ are as defined for a compound of formula (I), is treated:

either with an acid or a functional derivative of this acid of formula:

HOOC—$R_2$ (III)

in which $R_2$ is as defined for a compound of formula (I), when a compound of formula (I) is to be prepared in which —X— represents a —CO— group;

or with a sulfonyl halide of formula:

Hal-$SO_2$—$R_2$ (IV)

in which $R_2$ is as defined for a compound of formula (I) and Hal represents a halogen atom, preferentially chlorine, when a compound of formula (I) is to be prepared in which —X— represents an —$SO_2$— group;

or with a haloformate of formula:

HalCOOAr (V)

in which Hal represents a halogen atom and Ar represents a phenyl or a 4-nitrophenyl, to obtain an intermediate compound of formula:

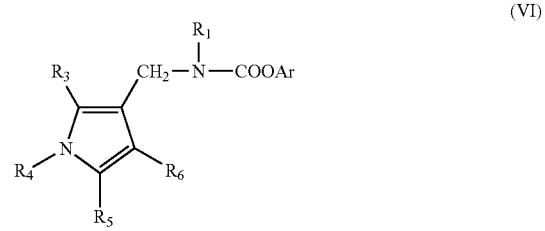

(VI)

in which $R_1$, $R_3$, $R_4$, $R_5$ and $R_6$ are as defined for a compound of formula (I), which is then reacted with an amine of formula:

HN($R_7$)$R_2$ (VII)

in which $R_2$ and $R_7$ are as defined for a compound of formula (I), when a compound of formula (I) is to be prepared in which —X— represents a group —CON($R_7$)—;

or with an isothiocyanate of formula $R_2$N=C=S (VIII), when a compound of formula (I) is to be prepared in which —X— represents a —CSNH— group.

Where appropriate, a compound of formula (IC) or (ID) in which $R_7$ represents a ($C_1$-$C_4$)alkyl group may be prepared via an alkylation reaction on the corresponding compound of formula (I) in which $R_7$ represents a hydrogen atom.

Optionally, the compound of formula (I) is converted into an acid-addition salt thereof.

When a compound of formula (II) is treated with the acid of formula (III) itself, the process is performed in the presence of a coupling agent used in peptide chemistry, such as 1,3-dicyclohexylcarbodiimide (DCC) or benzotriazol-1-yloxytris(dimethylamino)phosphonium (BOP) hexafluorophosphate or benzotriazol-1-yloxytris(pyrrolidino)phosphonium (PyBOP) hexafluorophosphate or 2-(1H-benzotriazol-1-yl)-1,1,3,3-tetramethyluronium tetrafluoroborate, in the presence of a base such as triethylamine, N,N-diisopropylethylamine or 4-dimethylaminopyridine, in a solvent such as dichloromethane, dichloroethane, N,N-dimethylformamide or tetrahydrofuran, at a temperature of between −10° C. and the reflux temperature of the solvent.

As functional derivative of the acid (III), it is possible to use the acid chloride, the anhydride, a mixed anhydride, a $C_1$-$C_4$ alkyl ester in which the alkyl is straight or branched, and an activated ester, for example p-nitrophenyl ester.

Thus, in the process according to the invention, the acid chloride obtained by reacting thionyl chloride or oxalyl chloride with the acid of formula (III), can be reacted with the compound of formula (II), in a solvent, such as a chlorinated solvent (for example dichloromethane, dichloroethane or chloroform), an ether (for example tetrahydrofuran or dioxane) or an amide (for example N,N-dimethylformamide), under an inert atmosphere, at a temperature of between 0° C. and room temperature, in the presence of a tertiary amine such as triethylamine, N-methylmorpholine or pyridine.

One variant consists in preparing the mixed anhydride of the acid of formula (III) by reacting ethyl chloroformate with the acid of formula (III), in the presence of a base such as triethylamine, and in reacting it with the compound of formula (II), in a solvent such as dichloromethane, under an inert atmosphere, at room temperature, in the presence of a base such as triethylamine.

When a compound of formula (II) is treated with a sulfonyl halide of formula (IV), the process is performed in the presence of a base such as triethylamine or diisopropylethylamine, in a solvent such as dichloromethane or tetrahydrofuran and at a temperature of between room temperature and the reflux temperature of the solvent.

When a compound of formula (II) is treated with a haloformate of formula (V), the process is performed in the presence of a base such as triethylamine, in a solvent such as dichloromethane and at a temperature of between 0° C. and room temperature. The intermediate compound of formula (VI) thus obtained is then reacted with an amine of formula (VII), in a solvent such as dichloromethane, in the presence of a base such as triethylamine and at a temperature of between 0° C. and the reflux temperature of the solvent.

According to one variant of the process, the compounds of formula (I) in which —X— represents a group —CON($R_7$)— in which $R_7$=H, may be prepared by reacting a compound of formula (II) with an isocyanate of formula $R_2$—N=C=O (IX), in the presence of a base such as triethylamine, in a solvent such as dichloromethane and at a temperature of between room temperature and the reflux temperature of the solvent.

According to another variant of the process, the compounds of formula (I) in which —X— represents a group —CON($R_7$)— may be prepared by reacting a compound of formula (II) with a compound of formula ClCON($R_7$)$R_2$ (IX) in the presence of a base such as triethylamine, in a solvent such as dichloromethane and at a temperature of between 0° C. and room temperature.

According to another variant of the process, a compound of formula (I) in which $R_1$ represents a ($C_1$-$C_3$)alkyl may also be prepared by reacting a compound of formula (I) in which $R_1$=H with a ($C_1$-$C_3$)alkyl halide, in the presence of a base such as sodium hydride, in a solvent such as N,N-dimethylformamide and at a temperature of between room temperature and the reflux temperature of the solvent.

The compounds of formula (I) thus obtained may be subsequently separated from the reaction medium and purified according to the standard methods, for example by crystallization or chromatography.

The compounds of formula (II) may be prepared according to the following reaction scheme:

SCHEME 1

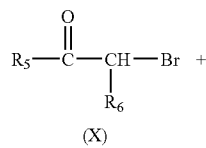

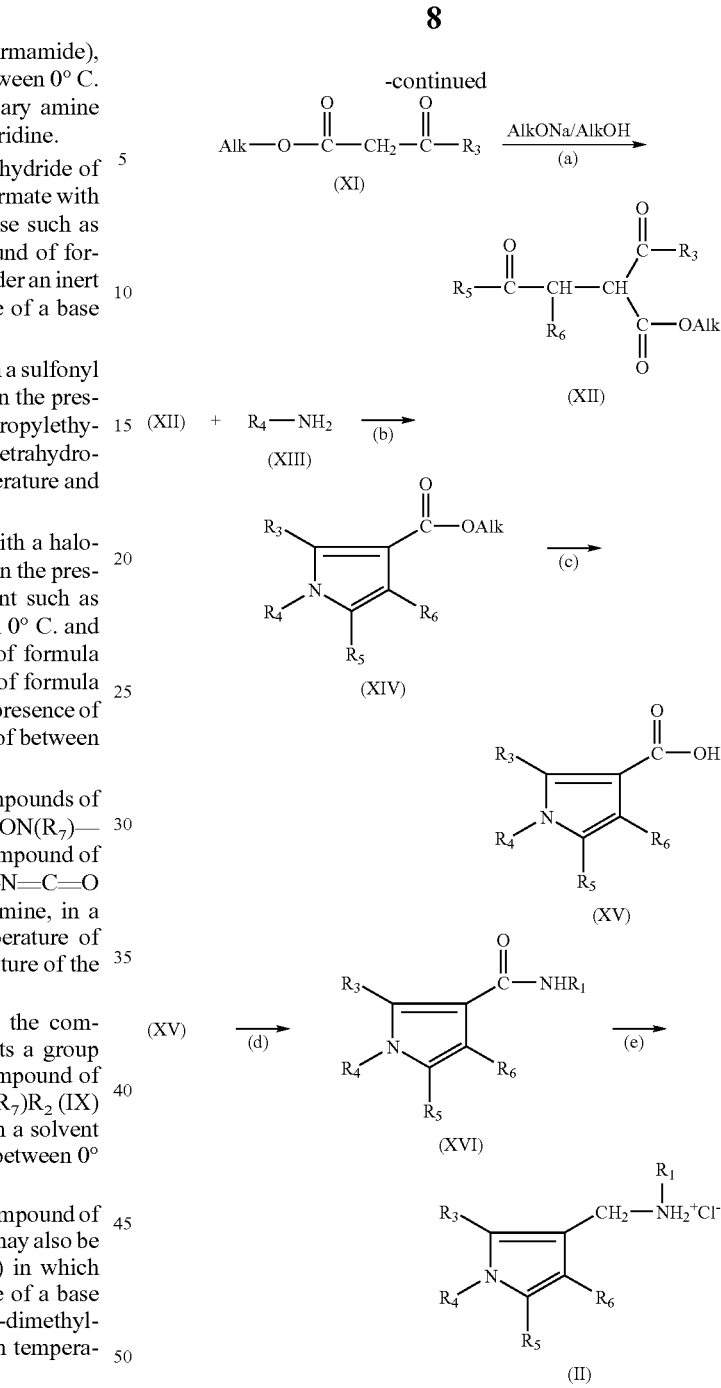

Step (a) is performed in the presence of a metal alkoxide in an alcohol, for example in the presence of sodium ethoxide in ethanol or in a mixture of ethanol and toluene at 0° C.

In step (b), the addition of the amine of formula (XIII) is performed in a protic solvent, for example an alcoholic solvent, at a temperature of between room temperature and the reflux temperature of the solvent. The ester obtained, of formula (XIV), is hydrolyzed in basic medium, in step (c); next, in step (d), the acid thus obtained of formula (XV) is treated with an amine $NH_2R_1$ or with ammonia gas when $R_1$=H, in a polar aprotic solvent, such as DMF or acetonitrile, in the presence of a coupling agent such as CDI (1,1'-carbonylbis (1H-imidazole)) or 1,3-dicyclohexylcarbodiimide (DCC) or benzotriazol-1-yloxytris(dimethylamino)phosphonium (BOP) hexafluorophosphate or benzotriazol-1-yloxytris(pyrrolidino)phosphonium (PyBOP) hexafluorophosphate. In step (e), the reduction of the carboxyamide function of the compound of formula (XVI) is performed using a reducing agent such as borane or lithium aluminum hydride, in a solvent such as tetrahydrofuran or iso ether, at a temperature of between room temperature and the reflux temperature of the solvent, followed by an acid hydrolysis.

The compounds of formula (II) in which $R_6$ is hydrogen are novel and constitute a further aspect of the present invention. Thus, a subject of the present invention is also the compounds of formula:

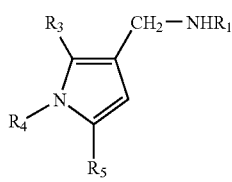

(II a)

in which:
- $R_1$ represents a hydrogen atom or a $(C_1-C_3)$alkyl group;
- $R_3$ represents a $(C_1-C_5)$alkyl or a $(C_3-C_7)$cycloalkyl;
- $R_4$ represents a phenyl, which is unsubstituted or substituted one or more times with substituents independently chosen from a halogen atom, a $(C_1-C_4)$alkyl, a $(C_1-C_4)$alkoxy, a trifluoromethyl radical and a group $S(O)_m$Alk;
- $R_5$ represents a phenyl, which is unsubstituted or substituted one or more times with substituents independently chosen from a halogen atom, a $(C_1-C_4)$alkyl, a $(C_1-C_4)$alkoxy, a trifluoromethyl radical and a group $S(O)_m$Alk;
- m in represents 0, 1 or 2;
- Alk represents a $(C_1-C_4)$alkyl.

Most particularly, the present invention relates to the compounds of formula:

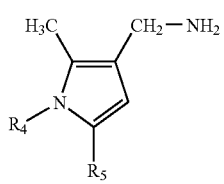

(II b)

in which:
- $R_4$ and $R_5$ represent, independently of each other, a 2,4-dichlorophenyl and a 4-chlorophenyl or a 2,4-dichlorophenyl and a 4-bromophenyl or a 2,4-dichlorophenyl and a 4-methoxyphenyl.

The compounds of formula (III) are known.

The compounds of formula (IV) are commercially available or described in the literature, or may be prepared according to methods described therein such as in J. Org. Chem. USSR, 1970, 6, 2454-2458; J. Am. Chem. Soc., 1952, 74, 2008; J. Med. Chem., 1977, 20(10), 1235-1239; EP0469 984; WO95/18105.

For example, the compounds of formula (IV) may be prepared by halogenation of the corresponding sulfonic acids or of salts thereof, for example of the sodium or potassium salts thereof. The reaction is performed in the presence of a halogenating agent such as phosphorus oxychloride, thionyl chloride, phosphorus trichloride, phosphorus tribromide or phosphorus pentachloride, without a solvent or in a solvent such as a halogenated hydrocarbon or N,N-dimethylformamide and at a temperature of between −10° C. and 200° C.

The compounds of formulae (V), (VII), (VIII) and (IX) are known or are prepared according to known methods.

The EXAMPLES that follow describe the preparation of certain compounds in accordance with the invention. These examples are non-limiting and serve merely to illustrate the present invention. The numbers of the illustrated compounds refer to those given in TABLE I below, which illustrates the chemical structures and physical properties of a number of compounds according to the invention.

In the Preparations and in the Examples, the following abbreviations are used:
- ether: diethyl ether
- iso ether: diisopropyl ether
- DMSO: dimethyl sulfoxide
- DMF: N,N-dimethylformamide
- THF: tetrahydrofuran
- TBTU: 2-(1H-benzotriazol-1-yl)-1,1,3,3-tetramethyluronium tetrafluoroborate
- DCM: dichloromethane
- EtOAc: ethyl acetate
- DIPEA: diisopropylethylamine
- LAH: Lithium aluminum hydride
- DBU: 1,8-diazabicyclo[5,4,0]undec-7-ene
- TFA: trifluoroacetic acid
- 2N hydrochloric ether: 2N solution of hydrogen chloride in diethyl ether
- m.p.: melting point
- RT: room temperature
- b.p.: boiling point
- HPLC: high performance liquid chromatography
- Silica H: silica 60H gel sold by Merck (DARMSTADT)
- pH 2 buffer solution: solution of 16.66 g of $KHSO_4$ and 32.32 g of $K_2SO_4$ in 1 liter of water.

The proton nuclear magnetic resonance ($^1$H NMR) spectra are recorded at 200 MHz in DMSO-$d_6$. The chemical shifts δ are expressed in parts per million (ppm). For the interpretation of the spectra, the following abbreviations are used: s: singlet, d: doublet, t: triplet, q: quartet, m: unresolved complex, mt: multiplet, bs: broad singlet, dd: doubled doublet.

The compounds according to the invention are analyzed by LC/UV/MS (liquid chromatography/UV detection/mass spectrometry) coupling. The molecular peak (MH$^+$) and the retention time (rt) in minutes are measured.

Conditions A:

A Symmetry C18 column of 2.1×50 mm, 3.5 μm is used, at 30° C., flow rate 0.4 ml/minute.

The eluent is composed as follows:
- solvent A: 0.005% trifluoroacetic acid (TFA) in water at pH 3.15;
- solvent B: 0.005% TFA in acetonitrile.

| | Gradient: | |
|---|---|---|
| Time (minutes) | % A | % B |
| 0 | 100 | 0 |
| 10 | 10 | 90 |
| 15 | 10 | 90 |
| 16 | 100 | 0 |
| 20 | 100 | 0 |

The UV detection is performed at λ=210 nM and the mass detection in positive ESI chemical ionization mode.

Conditions MS 5

An XTERRA MS C18 column of 2.1×30 mm, 3.5 μm is used, flow rate 1 ml/minute.

The eluent is composed as follows:
Solvent A: 0.025% TFA in water,
Solvent B: 0.025% TFA in acetonitrile.

| Gradient: | | |
|---|---|---|
| Time (minutes) | % A | % B |
| 0 | 100 | 0 |
| 2 | 0 | 100 |
| 2.7 | 0 | 100 |
| 2.75 | 100 | 0 |

The UV detection is performed with a diode array detector between 210 and 400 nm and the mass detection in positive ESI mode.

Conditions MS 2

An XTerra MS C18 column of 2.1×30 mm, 3.5 μm is used, at 30° C., flow rate 0.8 ml/minute.

The eluent is composed as follows:
solvent A: 0.025% trifluoroacetic acid (TFA) in water;
solvent B: 0.025% TFA in acetonitrile.

| Gradient: | | |
|---|---|---|
| Time (minutes) | % A | % B |
| 0 | 100 | 0 |
| 2 | 0 | 100 |
| 2.7 | 0 | 100 |
| 2.75 | 100 | 0 |

The UV detection is performed with a diode array detector between 210 and 400 (nm and the mass detection in positive ESI chemical ionization mode.

Preparations

Preparation 1

[1-(4-Chlorophenyl)-5-(2,4-dichlorophenyl)-2-methyl-1H-pyrrol-3-yl]methanaminium) chloride A) Ethyl 2-acetyl-4-oxo-4-(2,4-dichlorophenyl)butyrate To a solution of 3.26 ml of ethyl acetoacetate in ethanol (20 ml) is added dropwise 0.5 ml of a sodium ethoxide solution (21% in EtOH) at 0° C. The mixture is stirred for 15 minutes and 5.82 g de 2-bromo-1-(2,4-dichlorophenyl)ethanone pre-dissolved in 30 ml of an ethanol/toluene mixture (2/1; v/v) is then added. The mixture is stirred for 4 hours at RT and then concentrated to dryness. The residue is purified by chromatography on silica gel to give 3.8 g of liquid corresponding to the expected product.

B) Ethyl 1-(4-chlorophenyl)-5-(2,4-dichlorophenyl)-2-methyl-1H-pyrrol-3-carboxylate 10 g of the compound obtained in step A) are dissolved in 45 ml of anhydrous ethanol in the presence of 4.1 g of 4-chloroaniline. The mixture is heated at the reflux point of the ethanol for 3 days. After evaporating off the solvent, the expected product is crystallized from an isopropanol/ethanol mixture. 12.5 g of white crystals are obtained.

C) 1-(4-Chlorophenyl)-5-(2,4-dichlorophenyl)-2-methyl-1H-pyrrol-3-carboxylic acid 3.7 g of the ester obtained in the preceding step are dissolved in 180 ml of ethanol. 5 g of sodium hydroxide pellets are added portionwise, followed by 3 ml of water. The mixture is refluxed for 24 hours. After cooling, the crude material is concentrated and then dissolved in ethyl acetate. The organic phase is treated with saturated $K_2CO_3$ solution and then acidified with aqueous 10% HCl solution. After drying over $MgSO_4$, filtering and concentrating, 2.9 g of the expected compound are obtained in the form of a white solid.

D) 1-(4-Chlorophenyl)-5-(2,4-dichlorophenyl)-2-methyl-1H-pyrrol-3-carboxamide 20 g of the acid obtained in the preceding step and 9.7 g of 1,1'-carbonylbis(1H-imidazole) are dissolved in 250 ml of anhydrous DMF. The mixture is stirred for 1 hour at RT, and ammonia gas is then bubbled into the solution for 2 hours 30 minutes. After concentrating, the crude material is purified by chromatography on alumina gel. 16.9 g of a white solid corresponding to the expected amide are obtained.

LC/MS: $MH^+$=379, rt=9.82 (Conditions A).

E) [1-(4-Chlorophenyl)-5-(2,4-dichlorophenyl)-2-methyl-1H-pyrrol-3-yl]methanaminium chloride At 0° C., 200 ml of a solution of 14 g of the compound obtained in the preceding step in THF is added dropwise to a suspension of LAH in 200 ml of anhydrous THF. The mixture is then maintained at 60-70° C. for 30 minutes. After cooling, 10 ml of water are added. The solution is filtered and the filtrate is acidified with hydrochloric ether. After concentrating and oven-drying, 9.7 g of the expected compound are obtained in the form of a white solid.

NMR ($^1$H): 2.1 ppm: s: 3H, 3.9 ppm: s: 2H, 6.55 ppm: s: 1H; 7.05-7.55 ppm: m: 7H, 8.35 ppm: s: 3H.

LC/MS: $MH^+$=364, rt=9.04 (Conditions A).

Preparation 2

[1-(2,4-Dichlorophenyl)-5-(4-chlorophenyl)-2-methyl-1H-pyrrol-3-yl]methanaminium chloride. $MH^+$=364, rt=7.23 (Conditions A)

Preparation 3

[1-(4-Methoxyphenyl)-5-(2,4-dichlorophenyl)-2-methyl-1H-pyrrol-3-yl]methanaminium hydrochloride These compounds are obtained using a procedure similar to that described in Preparation 1.

The procedure below may also be used:

Preparation 4

1-(2,4-Dichlorophenyl)-5-(4-chlorophenyl)-2-methyl-1H-pyrrol-3-yl)methanaminium hydrochloride This compound is prepared according to the procedure described above for steps A, B, C and D. The final step is performed as follows:

A solution of 6.5 g of 1-(2,4-dichlorophenyl)-5-(4-chlorophenyl)-2-methyl-1H-pyrrol-3-carboxamide in 20 ml of TRF is brought to reflux, 5.3 ml of borohydridedimethyl sulfide complex are then added dropwise and refluxing is continued for 48 hours. The reaction medium is cooled to room temperature and 50 ml of methanol are added dropwise. The reaction medium is evaporated to dryness, 34 ml of a hydrochloric ether solution (1N) are then added dropwise and the mixture is stirred for 30 minutes at room temperature. The compound obtained is filtered off and washed with ether. 4.4 g of the expected compound are obtained.

EXAMPLE 1

Compound 1

N-((5-(4-(Chlorophenyl)-1-(2,4-dichlorophenyl)-2-methyl-1H-pyrrol-3-yl)-4-(trifluoromethyl)benzamide 0.9 g of the compound of Preparation 1 is dissolved in 28 ml of DCM, in the presence of 0.94 ml of triethylamine. 0.51 ml of 4-trifluoromethylbenzoyl chloride is added and the mixture is stirred for 24 hours at RT. The resulting mixture is evaporated to dryness and then purified by chromatography to give 0.6 g of the expected compound in solid form.

EXAMPLE 2

Compound 5

3-Chloro-N-((1-(4-chlorophenyl)-5-(2,4-dichlorophenyl)-2-methyl-1H-pyrrol-3-yl)methyl)benzenesulfonamide 0.9 g of the compound of Preparation 2 is dissolved in 20 ml of DCM in the presence of 0.74 ml of triethylamine, 0.58 mg of 3-chlorobenzenesulfonyl chloride is added and the mixture is stirred at RT for 20 hours. The reaction medium is poured into pentane. The expected compound precipitates out.

EXAMPLE 3

Compound 8

N-((1-(4-Chlorophenyl)-5-(2,4-dichlorophenyl)-2-methyl-1H-pyrrol-3-yl)methyl)-N'-(3-(trifluoromethyl)phenyl)urea 0.9 g of the compound of Preparation 2 is dissolved in 40 ml of DCM in the presence of 0.51 ml of triethylamine; 0.42 ml of 3-trifluoromethylbenzene isocyanate is added and the mixture is stirred at RT for 20 hours. The resulting mixture is purified by chromatography to give 0.9 g of the expected compound in solid form.

EXAMPLE 4

Certain compounds of formula (IA) in which —X—=—CO— are prepared by combinatorial chemistry, according to the process described below:

Carboxylic acids of formula (III) are dissolved in DMF to a concentration of 0.25 M in the presence of 3 equivalents of DIPEA. 120 μl of these solutions are placed in each 2 ml well and 120 ml of a solution of TBTU in DMF at a concentration of 0.25 M are added. 300 μl of a solution containing the methylamine of formula (II) in DMF at a concentration of 0.1 M and 3 equivalents of DIPEA are added to each well. The plates are shaken at RT for 16 hours and then evaporated. The products formed in each well are dissolved with 500 μl of EtOAc, 400 μl of 0.1 M $Na_2CO_3$ are then added and the plates are shaken. After separation of the phases by settling, 430 μl of aqueous phase are discarded, 300 μl of 5% NaCl are then added and the plates are shaken. 350 μl of aqueous phase are then discarded, 20 μl are taken for LC/UV/MS analysis and the rest is evaporated under vacuum to give the expected compound.

EXAMPLE 5

Certain compounds of formula (IB) in which —X—=—$SO_2$— are prepared by combinatorial chemistry according to the process described below:

The compounds of formula (II) are dissolved in DMF at a concentration of 0.1 M in the presence of 3 equivalents of DIPEA. 300 μl of these solutions are placed in each 2 ml well and 120 μl of a solution containing the corresponding sulfonyl chloride of formula (IV) in THF at a concentration of 0.25 M are added. The plates are shaken at RT for 16 hours and then evaporated. The products formed in each well are dissolved by adding 500 μl of EtOAc, 400 μl of 0.1 M $Na_2CO_3$ are added and the plates are shaken. After separation of the phases by settling, 430 μl of aqueous phase are discarded, 300 μl of 5% NaCl are added and the plates are shaken. After separation of the phases by settling, 350 μl of aqueous phase are discarded, 20 μl are taken for analysis by LC/UV/MS and the rest is evaporated under vacuum to give the expected compound.

EXAMPLE 6

Certain compounds of formula (IC) in which —X—=—CONH— are prepared by combinatorial chemistry according to the process described below:

The compounds of formula (II) are dissolved in DMF at a concentration of 0.1 M in the presence of 3 equivalents of DIPEA. 300 μl of these solutions are placed in each 2 ml well and 120 μl of a solution containing the corresponding isocyanate compound of formula (IX) in THF at a concentration of 0.25 M are added. The plates are shaken at RT for 16 hours. The products formed in each well are dissolved by adding 500 μl of EtOAc, 400 μl of 0.1 M $Na_2CO_3$ are added and the plates are shaken. After separation of the phases by settling, 430 μl of aqueous phase are discarded, 300 μl of 5% NaCl are added and the plates are shaken. After separation of the phases by settling, 350 μl of aqueous phase are discarded, 20 μl are taken for analysis by LC/UV/MS and the rest is evaporated under vacuum to give the expected compound.

EXAMPLE 7

The compounds of formula (ID) in which —X—=—CSNH— are prepared by combinatorial chemistry according to the process described below: The compounds of formula (II) are dissolved in DMF at a concentration of 0.1 M in the presence of 3 equivalents of DIPEA. 300 μl of these solutions are placed in each 2 ml well and 120 μl of a solution containing the corresponding isothiocyanate compound of formula (VIII) in THF at a concentration of 0.25 M are added. The plates are shaken at RT for 16 hours. The products formed in each well are dissolved by adding 500 μl of EtOAc, 400 μl of 0.1 M $Na_2CO_3$ are added and the plates are shaken. After separation of the phases by settling, 430 μl of aqueous phase are discarded, 300 μl of 5% NaCl are added and the plates are shaken. After separation of the phases by settling, 350 μl of aqueous phase are discarded, 20 μl are taken for analysis by LC/UV/MS and the rest is evaporated under vacuum to give the expected compound.

By working according to the above examples, the compounds according to the invention of formulae IA, IB, IC and ID, collated in Tables I, II, III and IV below, are prepared.

In these tables, Me, Et, Pr, iP and tBu represent, respectively, methyl, ethyl, propyl, isopropyl and tert-butyl groups.

TABLE I (IA)

Structure: pyrrole with Me at 2-position, CH$_2$NHCO—R$_2$ at 4-position, R$_4$ on N, R$_5$ at 5-position.

| Compound No. | R$_2$ | R$_4$ | R$_5$ | Characterization conditions |
|---|---|---|---|---|
| 1 | 4-CF$_3$-C$_6$H$_4$— | 2,4-diCl-C$_6$H$_3$— | 4-Cl-C$_6$H$_4$— | m.p. = 75° C.<br>MH$^+$ = 537<br>rt = 12.05<br>A |
| 2 | —CH(CH$_2$CH$_2$CH$_3$)$_2$ | 2,4-diCl-C$_6$H$_3$— | 4-Cl-C$_6$H$_4$— | m.p. = 155° C.<br>MH$^+$ = 491<br>rt = 12.32<br>A |
| 3 | 4-CF$_3$-C$_6$H$_4$— | 4-Cl-C$_6$H$_4$— | 2,4-diCl-C$_6$H$_3$— | m.p. = 75° C.<br>MH$^+$ = 537<br>rt = 12.05<br>A |
| 4* | 1H-indol-2-yl | 4-Cl-C$_6$H$_4$— | 2,4-diCl-C$_6$H$_3$— | m.p. = 105° C.<br>MH$^+$ = 508<br>rt = 11.38<br>A |
| 9 | 4-OCF$_3$-C$_6$H$_4$— | 2,4-diCl-C$_6$H$_3$— | 4-Cl-C$_6$H$_4$— | MH$^+$ = 553<br>rt = 2.11<br>MS 2 |
| 10 | Ph$_2$CH—CH$_2$— | 2,4-diCl-C$_6$H$_3$— | 4-Cl-C$_6$H$_4$— | MH$^+$ = 573<br>rt = 2.12<br>MS 2 |
| 11 | iPr- | 4-OMe-C$_6$H$_4$— | 2,4-diCl-C$_6$H$_3$— | MH$^+$ = 431<br>rt = 2.27<br>MS 5 |
| 12 | tBu- | 4-OMe-C$_6$H$_4$— | 2,4-diCl-C$_6$H$_3$— | MH$^+$ = 445<br>rt = 2.29<br>MS 5 |

TABLE I-continued
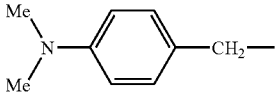
(IA)
| Compound No. | R₂ | R₄ | R₅ | Characterization conditions |
|---|---|---|---|---|
| 13 | 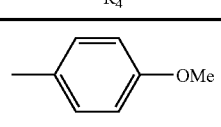 | 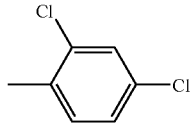 | 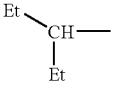 | MH⁺ = 522<br>rt = 2.01<br>MS 5 |
| 14 | 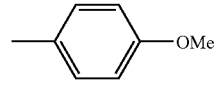 | 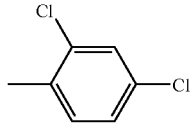 | 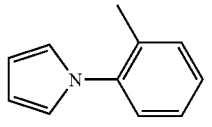 | MH⁺ = 459<br>rt = 2.34<br>MS 5 |
| 15 | 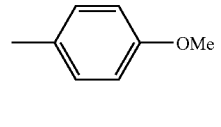 | 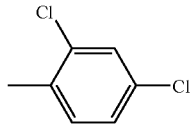 | 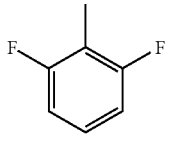 | MH⁺ = 530<br>rt = 2.41<br>MS 5 |
| 16 | 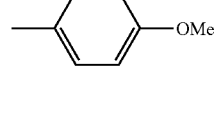 | 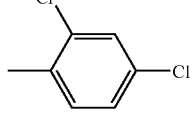 | 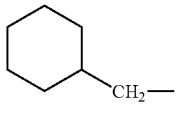 | MH⁺ = 501<br>rt = 2.32<br>MS 5 |
| 17 | 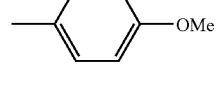 | 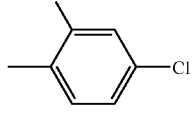 | 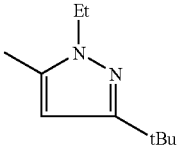 | MH⁺ = 485<br>rt = 2.42<br>MS 5 |
| 18 | 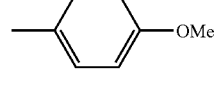 | 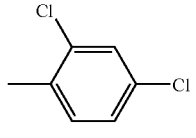 | 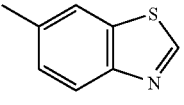 | MH⁺ = 539<br>rt = 2.5<br>MS 5 |
| 19 | 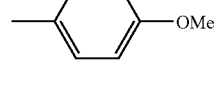 | 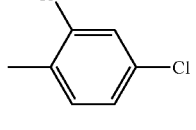 | 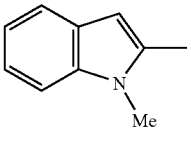 | MH⁺ = 522<br>rt = 2.29<br>MS 5 |
| 20 | 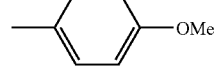 | 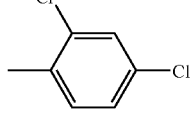 | 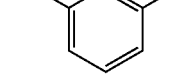 | MH⁺ = 518<br>rt = 2.47<br>MS 5 |
| 21 | 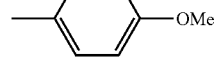 | 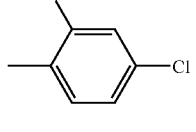 | | MH⁺ = 495<br>rt = 2.33<br>MS 5 |

TABLE I-continued (IA)

| Compound No. | R₂ | R₄ | R₅ | Characterization conditions |
|---|---|---|---|---|
| 22 | 3,5-dimethylphenyl | 4-methoxyphenyl | 2,4-dichlorophenyl | MH⁺ = 493<br>rt = 2.46<br>MS 5 |
| 23 | 2-methylindol-3-yl | 4-methoxyphenyl | 2,4-dichlorophenyl | MH⁺ = 504<br>rt = 2.4<br>MS 5 |
| 24 | 3-methoxycyclohexyl (methyl substituted) | 4-methoxyphenyl | 2,4-dichlorophenyl | MH⁺ = 501<br>rt = 2.31<br>MS 5 |
| 25 | cycloheptyl | 4-methoxyphenyl | 2,4-dichlorophenyl | MH⁺ = 485<br>rt = 2.42<br>MS 5 |
| 26 | 1-methylcyclohexyl | 4-methoxyphenyl | 2,4-dichlorophenyl | MH⁺ = 485<br>rt = 2.43<br>MS 5 |
| 27 | 4-(pyrrol-1-yl)phenyl | 4-methoxyphenyl | 2,4-dichlorophenyl | MH⁺ = 530<br>rt = 2.42<br>MS 5 |
| 28 | 4-methoxycyclohexyl | 4-methoxyphenyl | 2,4-dichlorophenyl | MH⁺ = 501<br>rt = 2.3<br>MS 5 |
| 29 | 1-(pyrrol-1-yl)-2,2-dimethylpropyl | 4-methoxyphenyl | 2,4-dichlorophenyl | MH⁺ = 524<br>rt = 2.47<br>MS 5 |
| 30 | 4-(trifluoromethyl)phenethyl | 4-methoxyphenyl | 2,4-dichlorophenyl | MH⁺ = 561<br>rt = 2.44<br>MS 5 |

TABLE I-continued
(IA)
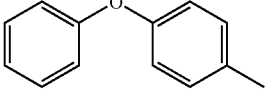
| Compound No. | R$_2$ | R$_4$ | R$_5$ | Characterization conditions |
|---|---|---|---|---|
| 31 | 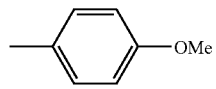 | 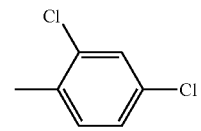 | 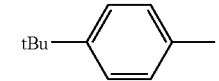 | MH$^+$ = 557<br>rt = 2.5<br>MS 5 |
| 32 | 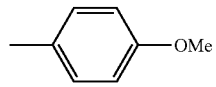 | 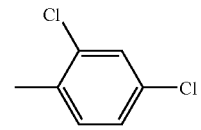 | 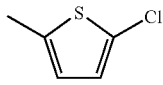 | MH$^+$ = 521<br>rt = 2.49<br>MS 5 |
| 33 | 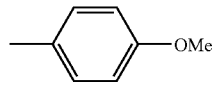 | 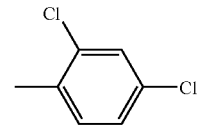 | 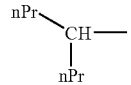 | MH$^+$ = 505<br>rt = 2.42<br>MS 5 |
| 34 | 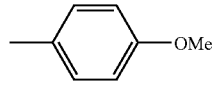 | 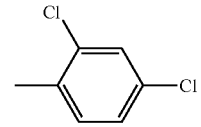 | 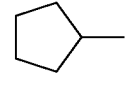 | MH$^+$ = 487<br>rt = 2.45<br>MS 5 |
| 35 | 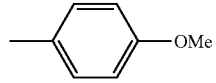 | 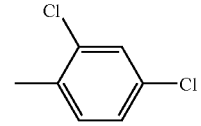 | 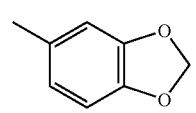 | MH$^+$ = 457<br>rt = 2.33<br>MS 5 |
| 36 | 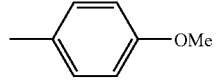 | 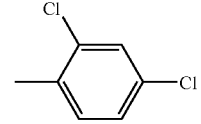 | 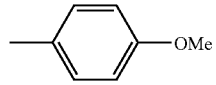 | MH$^+$ = 509<br>rt = 2.35<br>MS 5 |
| 37 | nBu- | 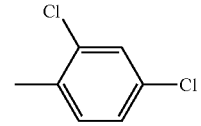 | 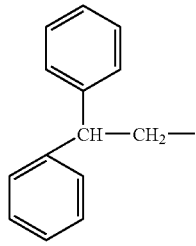 | MH$^+$ = 445<br>rt = 2.31<br>MS 5 |
| 38 | 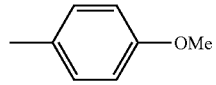 | 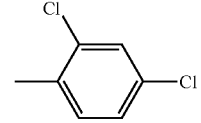 | 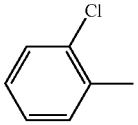 | MH$^+$ = 569<br>rt = 2.45<br>MS 5 |
| 39 | 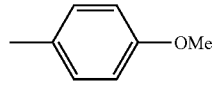 | 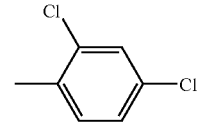 | | MH$^+$ = 499<br>rt = 2.34<br>MS 5 |

TABLE I-continued
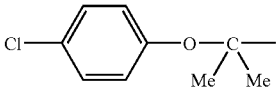
(IA)
| Compound No. | R₂ | R₄ | R₅ | Characterization conditions |
|---|---|---|---|---|
| 40 | 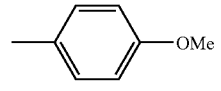 | 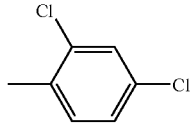 | 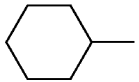 | MH⁺ = 557<br>rt = 2.55<br>MS 5 |
| 41 | 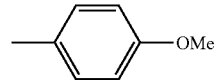 | 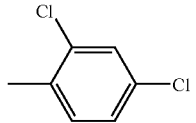 | 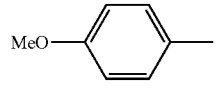 | MH⁺ = 471<br>rt = 2.4<br>MS 5 |
| 42 | 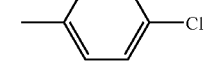 | 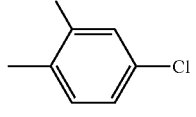 | 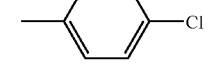 | MH⁺ = 499<br>rt = 7.84<br>MS 2 |
| 43 | iPr- | 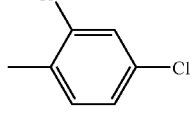 | 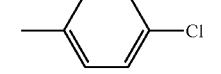 | MH⁺ = 435<br>rt = 7.53<br>MS 2 |
| 44 | tBu- | 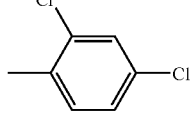 | 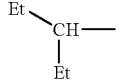 | MH⁺ = 449<br>rt = 1.95<br>MS 2 |
| 45 | 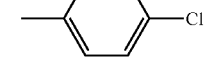 | 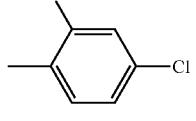 | 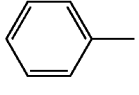 | MH⁺ = 463<br>rt = 2.05<br>MS 2 |
| 46 | 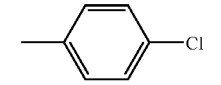 | 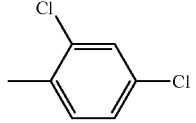 | 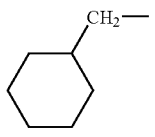 | MH⁺ = 469<br>rt = 7.88<br>MS 2 |
| 47 |  | 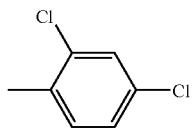 | 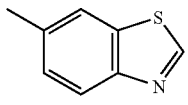 | MH⁺ = 489<br>rt = 2.13<br>MS 2 |
| 48 |  | 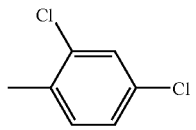 |  | MH⁺ = 526<br>rt = 7.66<br>MS 2 |

TABLE I-continued (IA)

| Compound No. | R₂ | R₄ | R₅ | Characterization conditions |
|---|---|---|---|---|
| 49 | 4-(NEt₂)-phenyl-methyl | 4-Cl-phenyl | 2,4-diCl-phenyl | MH⁺ = 540<br>rt = 1.89<br>MS 2 |
| 50 | 5-methyl-2,3-dihydrobenzofuran | 4-Cl-phenyl | 2,4-diCl-phenyl | MH⁺ = 511<br>rt = 7.85<br>MS 2 |
| 51 | cycloheptyl | 4-Cl-phenyl | 2,4-diCl-phenyl | MH⁺ = 489<br>rt = 8.41<br>MS 2 |
| 52 | 1-methylcyclohexyl | 4-Cl-phenyl | 2,4-diCl-phenyl | MH⁺ = 489<br>rt = 2.14<br>MS 2 |
| 53 | 4-(pyrrol-1-yl)phenyl-methyl | 4-Cl-phenyl | 2,4-diCl-phenyl | MH⁺ = 534<br>rt = 8.27<br>MS 2 |
| 54 | norbornyl | 4-Cl-phenyl | 2,4-diCl-phenyl | MH⁺ = 487<br>rt = 2.11<br>MS 2 |
| 55 | 1-propylbutyl (CH(nPr)₂) | 4-Cl-phenyl | 2,4-diCl-phenyl | MH⁺ = 491<br>rt = 2.15<br>MS 2 |
| 56 | 2,6-dimethoxy-3-methylpyridin-... | 4-Cl-phenyl | 2,4-diCl-phenyl | MH⁺ = 530<br>rt = 2.15<br>MS 2 |
| 57 | benzo[1,3]dioxol-5-yl-methyl | 4-Cl-phenyl | 2,4-diCl-phenyl | MH⁺ = 513<br>rt = 7.81<br>MS 2 |

TABLE I-continued
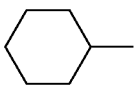
(IA)
| Compound No. | R$_2$ | R$_4$ | R$_5$ | Characterization conditions |
|---|---|---|---|---|
| 58 |  | 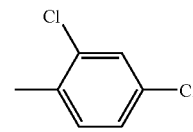 | 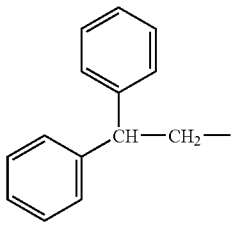 | MH$^+$ = 475<br>rt = 2.08<br>MS 2 |
| 59 |  | 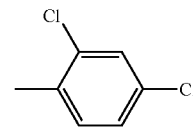 | 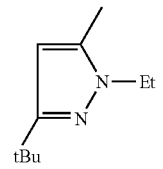 | MH$^+$ = 573<br>rt = 2.12<br>MS 2 |
| 60 |  | 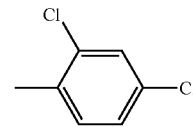 | 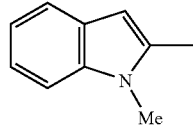 | MH$^+$ = 543<br>rt = 2.16<br>MS 2 |
| 61 |  | 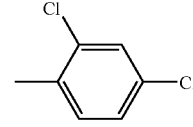 | 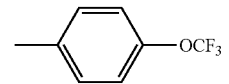 | MH$^+$ = 522<br>rt = 2.13<br>MS 2 |
| 62 |  | 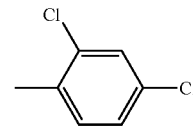 | 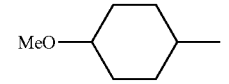 | MH$^+$ = 553<br>rt = 2.13<br>MS 2 |
| 63 |  | 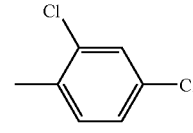 | 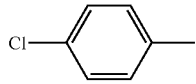 | MH$^+$ = 505<br>rt = 1.97<br>MS 2 |
| 64 |  | 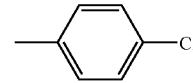 | 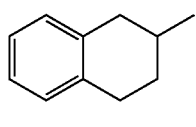 | MH$^+$ = 503<br>rt = 2.09<br>MS 2 |
| 65 | 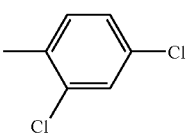 | 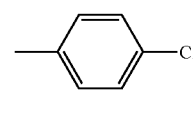 |  | MH$^+$ = 523<br>rt = 2.09<br>MS 2 |

TABLE I-continued (IA)

| Compound No. | R₂ | R₄ | R₅ | Characterization conditions |
|---|---|---|---|---|
| 66 | 4-Cl-phenyl | 4-Cl-phenyl | 2,4-diCl-phenyl | MH⁺ = 503<br>rt = 2.56<br>MS 5 |
| 67 | 1-(1-phenylethyl)pyrrol-2-yl | 4-Cl-phenyl | 2,4-diCl-phenyl | MH⁺ = 548<br>rt = 2.52<br>MS 2 |
| 68 | 1,2,3,4-tetrahydronaphthalen-2-yl | 4-Cl-phenyl | 2,4-diCl-phenyl | MH⁺ = 523<br>rt = 2.57<br>MS 5 |
| 69 | 3-cyanophenyl | 4-Cl-phenyl | 2,4-diCl-phenyl | MH⁺ = 494<br>rt = 2.47<br>MS 5 |
| 70 | CF₃C(Me)(OH)CH₂— | 4-Cl-phenyl | 2,4-diCl-phenyl | MH⁺ = 519<br>rt = 2.45<br>MS 5 |
| 71 | 4-CF₃-phenyl | 4-Cl-phenyl | 2,4-diCl-phenyl |  |
| 72 | benzyl | 4-Cl-phenyl | 2,4-diCl-phenyl | MH⁺ = 483<br>rt = 2.43<br>MS 5 |

*The compounds numbered 5 to 8 are described in Tables II and III below.

TABLE II (IB)

Structure: Pyrrole with Me at 2-position, CH₂NHSO₂—R₂ at 3-position, R₄ on N, R₅ at 5-position.

| Compound No. | R₂ | R₄ | R₅ | Characterization conditions |
|---|---|---|---|---|
| 5 | 3-chlorophenyl | 4-chlorophenyl | 2,4-dichlorophenyl | m.p. = 128° C.<br>MH⁺ = 539<br>rt = 12.07<br>A |
| 6 | —CH₂-(3-trifluoromethylphenyl) | 4-chlorophenyl | 2,4-dichlorophenyl | m.p. = 63° C.<br>MH⁺ = 587<br>rt = 12.15<br>A |
| 73 | 3,5-difluorophenyl | 3,4-dichlorophenyl | 4-chlorophenyl | MH⁺ = 541<br>rt = 2.47<br>MS 5 |
| 74 | 2-thienyl | 3,4-dichlorophenyl | 4-chlorophenyl | MH⁺ = 511<br>rt = 2.41<br>MS 5 |
| 75 | 2-fluorophenyl | 3,4-dichlorophenyl | 4-chlorophenyl | MH⁺ = 523<br>rt = 2.43<br>MS 5 |
| 76 | 5-trifluoromethyl-2,4-dimethylfuran-3-yl | 3,4-dichlorophenyl | 4-chlorophenyl | MH⁺ = 577<br>rt = 2.52<br>MS 5 |
| 77 | 3-methoxyphenyl | 3,4-dichlorophenyl | 4-chlorophenyl | MH⁺ = 535<br>rt = 2.49<br>MS 5 |
| 78 | 3-fluorophenyl | 3,4-dichlorophenyl | 4-chlorophenyl | MH⁺ = 523<br>rt = 2.47<br>MS 5 |

TABLE II-continued
(IB)
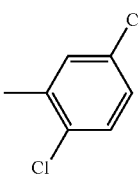
| Compound No. | R$_2$ | R$_4$ | R$_5$ | Characterization conditions |
|---|---|---|---|---|
| 79 | 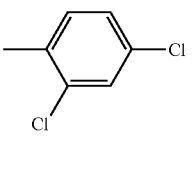 | 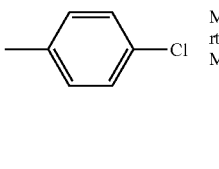 | 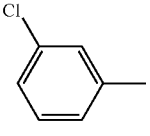 | MH$^+$ = 573<br>rt = 2.55<br>MS 5 |
| 80 | 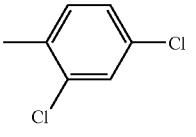 | 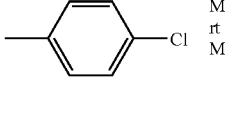 | 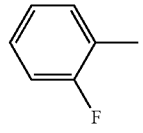 | MH$^+$ = 538<br>rt = 2.54<br>MS 5 |
| 81 | 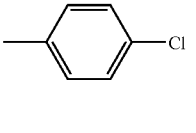 | 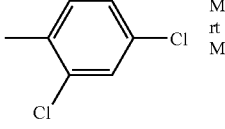 | 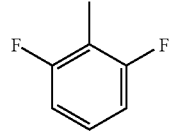 | MH$^+$ = 523<br>rt = 2.04<br>MS 2 |
| 82 | 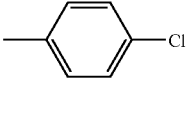 | 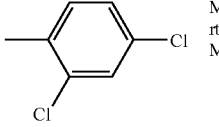 | 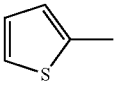 | MH$^+$ = 541<br>rt = 2.16<br>MS 2 |
| 83 | 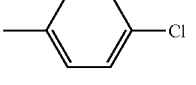 | 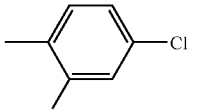 | 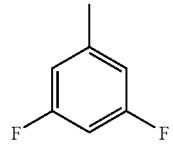 | |
| 84 | 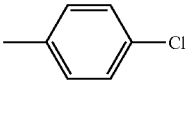 | 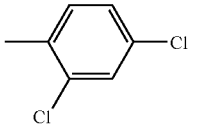 | 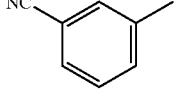 | |
| 85 | 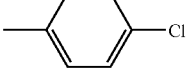 | 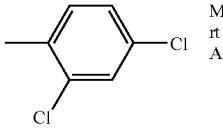 | 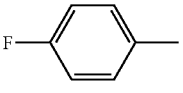 | MH$^+$ = 530<br>rt = 11.57<br>A |
| 86 | 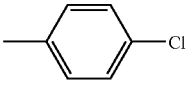 | 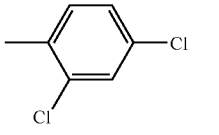 | 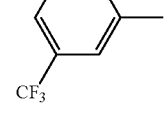 | |
| 87 | 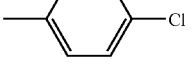 | 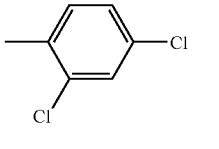 | | |

TABLE II-continued
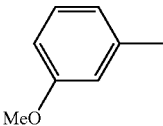
(IB)
| Compound No. | R₂ | R₄ | R₅ | Characterization conditions |
|---|---|---|---|---|
| 88 | 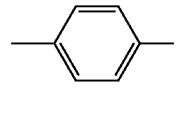 | 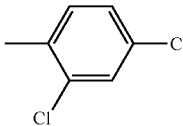 | 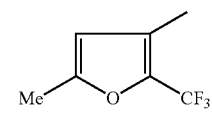 | MH⁺ = 536<br>rt = 11.93<br>A |
| 89 | 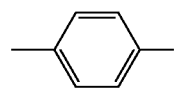 | 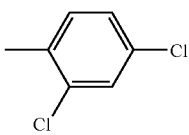 | 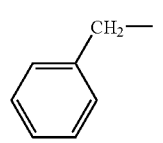 | |
| 90 | 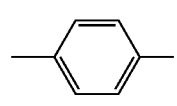 | 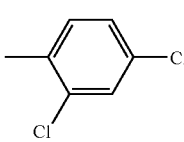 | 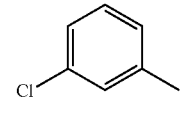 | MH⁺ = 519<br>rt = 2.05<br>MS 2 |
| 91 | 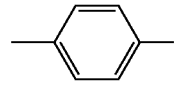 | 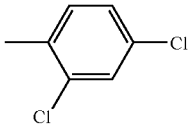 | 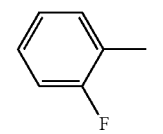 | |
| 92 | 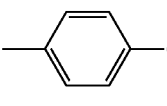 | 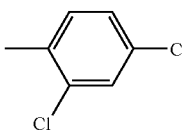 | 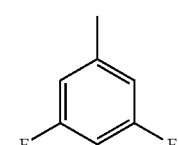 | MH⁺ = 519<br>rt = 2.08<br>MS 5 |
| 93 | 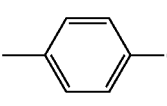 | 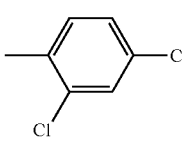 | 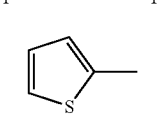 | MH⁺ = 537<br>rt = 2.1<br>MS 5 |
| 94 | 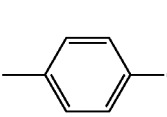 | 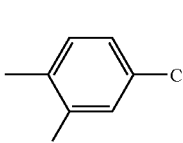 | 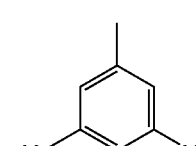 | MH⁺ = 507<br>rt = 2.06<br>MS 5 |
| 95 | 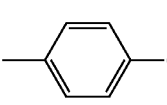 | 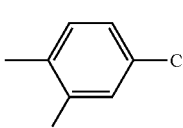 | 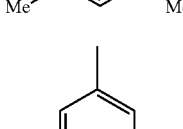 | MH⁺ = 529<br>rt = 2.22<br>MS 5 |
| 96 | 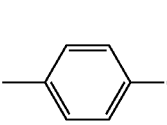 | | 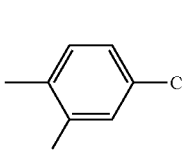 | MH⁺ = 537<br>rt = 2.13<br>MS 5 |

TABLE II-continued
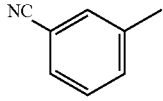
(IB)
| Compound No. | R$_2$ | R$_4$ | R$_5$ | Characterization conditions |
|---|---|---|---|---|
| 97 | 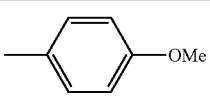 | 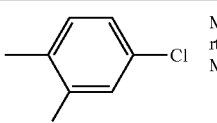 | 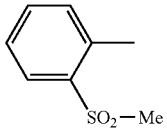 | MH$^+$ = 526<br>rt = 2.08<br>MS 5 |
| 98 | 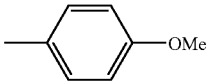 | 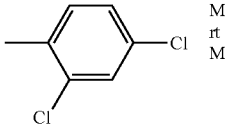 | 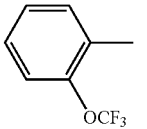 | MH$^+$ = 579<br>rt = 2.08<br>MS 5 |
| 99 | 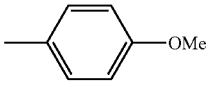 | 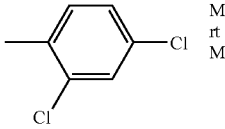 | 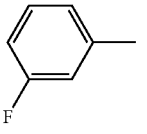 | MH$^+$ = 585<br>rt = 2.18<br>MS 5 |
| 100 | 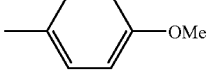 | 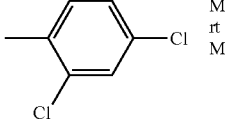 | 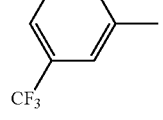 | MH$^+$ = 519<br>rt = 2.12<br>MS 5 |
| 101 | 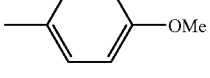 | 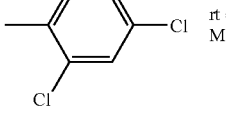 | 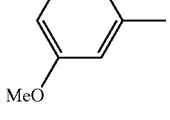 | MH$^+$ = 569<br>rt = 2.18<br>MS 5 |
| 102 | 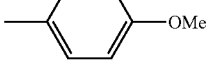 | 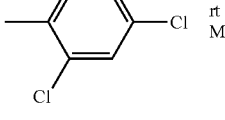 | 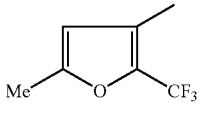 | MH$^+$ = 531<br>rt = 2.11<br>MS 5 |
| 103 | 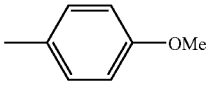 | 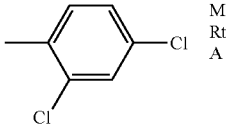 | 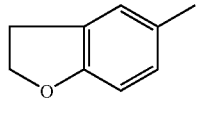 | MH$^+$ = 574<br>Rt = 11.92<br>A |
| 104 | 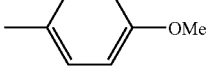 | 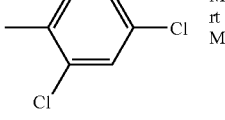 | 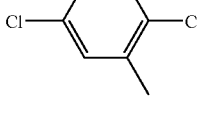 | MH$^+$ = 543<br>rt = 2.06<br>MS 5 |
| 105 | 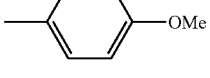 | 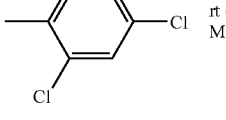 | 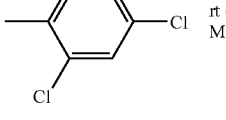 | MH$^+$ = 569<br>rt = 2.18<br>MS 5 |

TABLE II-continued (IB)

| Compound No. | R$_2$ | R$_4$ | R$_5$ | Characterization conditions |
|---|---|---|---|---|
| 106 | 7-methyl-2,3-dihydro-1,4-benzodioxine | 4-OMe-phenyl | 2,4-dichlorophenyl | MH$^+$ = 559<br>rt = 2.04<br>MS 5 |
| 107 | benzyl (PhCH$_2$-) | 4-OMe-phenyl | 2,4-dichlorophenyl | MH$^+$ = 515<br>rt = 2.14<br>MS 5 |
| 108 | 3-chlorophenyl | 4-OMe-phenyl | 2,4-dichlorophenyl | MH$^+$ = 535<br>rt = 2.18<br>MS 5 |
| 109 | 2-CF$_3$-phenyl | 4-OMe-phenyl | 2,4-dichlorophenyl | MH$^+$ = 569<br>rt = 2.15<br>MS 5 |
| 110 | phenyl | 2,4-dichlorophenyl | 4-chlorophenyl | |
| 111 | 3-CF$_3$-phenyl | 2,4-dichlorophenyl | 4-chlorophenyl | |

TABLE III (IC)

| Compound No. | R₂ | R₄ | R₅ | Characterization conditions |
|---|---|---|---|---|
| 7 | 2-biphenyl | 4-Cl-phenyl | 2,4-diCl-phenyl | m.p. = 90° C.<br>MH⁺ = 560<br>rt = 11.52<br>A |
| 8 | 3-CF₃-phenyl | 4-Cl-phenyl | 2,4-diCl-phenyl | m.p. = 92° C.<br>MH⁺ = 552<br>rt = 12.12<br>A |
| 112 | 4-Cl-phenyl | 2,4-diCl-phenyl | 4-Cl-phenyl | MH⁺ = 518<br>rt = 2.44<br>MS 5 |
| 113 | 4-F-phenyl | 4-Cl-phenyl | 2,4-diCl-phenyl | MH⁺ = 502<br>rt = 2.03<br>MS 2 |
| 114 | 2-OMe-phenyl | 4-Cl-phenyl | 2,4-diCl-phenyl | MH⁺ = 514<br>rt = 2.04<br>MS 2 |
| 115 | 4-Br-phenyl | 4-Cl-phenyl | 2,4-diCl-phenyl | MH⁺ = 562<br>rt = 2.11<br>MS 2 |

TABLE III-continued (IC)

| Compound No. | R₂ | R₄ | R₅ | Characterization conditions |
|---|---|---|---|---|
| 116 | benzyl (PhCH₂—) | 4-Cl-phenyl | 2,4-diCl-phenyl | MH⁺ = 498<br>rt = 1.99<br>MS 2 |
| 117 | 3-OMe-phenyl | 4-Cl-phenyl | 2,4-diCl-phenyl | MH⁺ = 514<br>rt = 2.01<br>MS 2 |
| 118 | 3-F-benzyl | 4-Cl-phenyl | 2,4-diCl-phenyl | MH⁺ = 516<br>rt = 2.00<br>MS 2 |
| 119 | phenyl | 4-Cl-phenyl | 2,4-diCl-phenyl | MH⁺ = 484<br>rt = 2.01<br>MS 2 |
| 120 | 3-F-phenyl | 4-Cl-phenyl | 2,4-diCl-phenyl | MH⁺ = 502<br>rt = 2.05<br>MS 2 |
| 121 | cyclohexyl | 4-Cl-phenyl | 2,4-diCl-phenyl | MH⁺ = 490<br>rt = 2.04<br>MS 2 |

TABLE III-continued (IC)

Me—[pyrrole]—CH₂NHCONH—R₂ with R₄ on N, R₅ at position 5

| Compound No. | R₂ | R₄ | R₅ | Characterization conditions |
|---|---|---|---|---|
| 122 | furan-2-yl-CH₂— | 4-Cl-phenyl | 2,4-diCl-phenyl | MH⁺ = 488<br>rt = 1.93<br>MS 2 |
| 123 | 3-Cl-phenyl | 4-Cl-phenyl | 2,4-diCl-phenyl | MH⁺ = 518<br>rt = 2.1<br>MS 2 |
| 124 | 2-F-benzyl | 4-Cl-phenyl | 2,4-diCl-phenyl | MH⁺ = 516<br>rt = 2.00<br>MS 2 |
| 125 | 3,5-diMeO-phenyl | 4-Cl-phenyl | 2,4-diCl-phenyl | MH⁺ = 544<br>rt = 2.02<br>MS 2 |
| 126 | 3-MeO-phenyl | 4-MeO-phenyl | 2,4-diCl-phenyl | MH⁺ = 510<br>rt = 2.09<br>MS 5 |
| 127 | 4-MeO-phenyl | 4-MeO-phenyl | 2,4-diCl-phenyl | MH⁺ = 510<br>rt = 2.05<br>MS 5 |

TABLE III-continued (IC)

Structure: pyrrole with Me at 2-position, R4 on N, R5 at 5-position, and CH₂NHCONH—R₂ at 3-position.

| Compound No. | R₂ | R₄ | R₅ | Characterization conditions |
|---|---|---|---|---|
| 128 | 4-Cl-phenyl | 4-MeO-phenyl | 2,4-dichlorophenyl | MH⁺ = 514<br>rt = 2.12<br>MS 5 |
| 129 | 2,5-difluorophenyl | 4-MeO-phenyl | 2,4-dichlorophenyl | MH⁺ = 516<br>rt = 2.13<br>MS 5 |
| 130 | tBu- | 4-MeO-phenyl | 2,4-dichlorophenyl | MH⁺ = 460<br>rt = 2.03<br>MS 5 |
| 131 | 3-F-benzyl (CH₂—) | 4-MeO-phenyl | 2,4-dichlorophenyl | MH⁺ = 512<br>rt = 2.02<br>MS 5 |
| 132 | phenyl | 4-MeO-phenyl | 2,4-dichlorophenyl | MH⁺ = 480<br>rt = 2.09<br>MS 5 |
| 133 | 3-F-phenyl | 4-MeO-phenyl | 2,4-dichlorophenyl | MH⁺ = 498<br>rt = 2.08<br>MS 5 |
| 134 | cyclohexyl | 4-MeO-phenyl | 2,4-dichlorophenyl | MH⁺ = 486<br>rt = 2.10<br>MS 5 |

TABLE III-continued
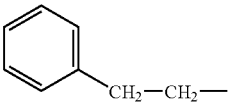
(IC)
| Compound No. | R₂ | R₄ | R₅ | Characterization conditions |
|---|---|---|---|---|
| 135 | 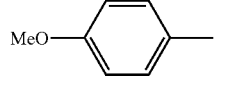 | 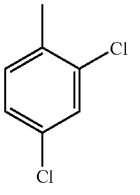 | 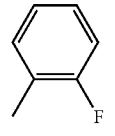 | MH⁺ = 508<br>rt = 2.07<br>MS 5 |
| 136 | 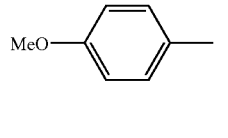 | 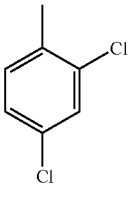 | 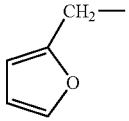 | MH⁺ = 498<br>rt = 2.11<br>MS 5 |
| 137 | 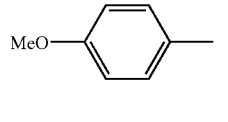 | 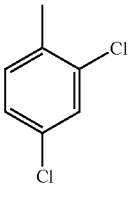 | 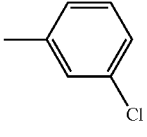 | MH⁺ = 484<br>rt = 1.99<br>MS 5 |
| 138 | 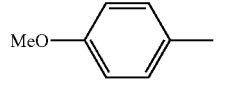 | 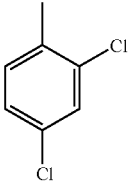 | 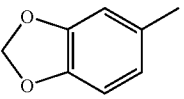 | MH⁺ = 514<br>rt = 2.14<br>MS 5 |
| 139 | 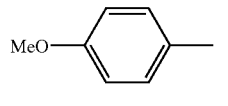 | 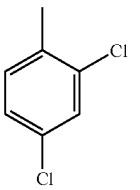 | 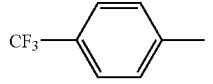 | MH⁺ = 524<br>rt = 2.06<br>MS 5 |
| 140 | 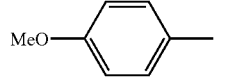 | 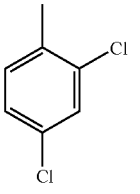 | | MH⁺ = 548<br>rt = 2.2<br>MS 5 |

TABLE III-continued (IC)

Structure: Pyrrole with Me at 2-position, CH$_2$NHCONH—R$_2$ at 4-position, R$_4$ on N, R$_5$ at 5-position.

| Compound No. | R$_2$ | R$_4$ | R$_5$ | Characterization conditions |
|---|---|---|---|---|
| 141 | 1-methyl-tetrahydronaphthalen-1-yl | 4-MeO-phenyl | 2,4-diCl-phenyl | MH$^+$ = 534<br>rt = 2.14<br>MS 5 |
| 142 | 3,5-diF-4-methylphenyl | 4-MeO-phenyl | 2,4-diCl-phenyl | MH$^+$ = 516<br>rt = 2.17<br>MS 5 |
| 143 | 2-F-benzyl | 4-MeO-phenyl | 2,4-diCl-phenyl | MH$^+$ = 512<br>rt = 2.02<br>MS 5 |
| 144 | 3-MeO-5-OMe-4-methylphenyl | 4-MeO-phenyl | 2,4-diCl-phenyl | MH$^+$ = 540<br>rt = 2.07<br>MS 5 |
| 145 | 4-Me-phenyl | 4-MeO-phenyl | 2,4-diCl-phenyl | MH$^+$ = 494<br>rt = 2.10<br>MS 5 |
| 146 | 3-Cl-phenyl | 2,4-diCl-phenyl | 4-Cl-phenyl | MH$^+$ = 518<br>rt = 2.09<br>MS 2 |
| 147 | 4-Cl-phenyl | 4-Cl-phenyl | 2,4-diCl-phenyl | MH$^+$ = 518<br>rt = 2.09<br>MS 2 |

TABLE III-continued
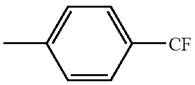
(IC)
| Compound No. | R₂ | R₄ | R₅ | Characterization conditions |
|---|---|---|---|---|
| 148 | 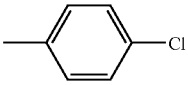 | 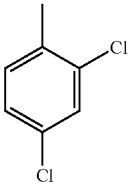 | 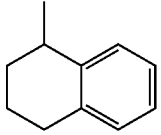 | MH⁺ = 552<br>rt = 2.11<br>MS 2 |
| 149 |  | 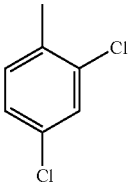 | 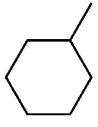 | MH⁺ = 538<br>rt = 2.09<br>MS 2 |
TABLE IV
(ID)
| Compound No. | R₂ | R₄ | R₅ | Characterization conditions |
|---|---|---|---|---|
| 150 | 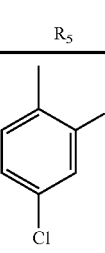 | 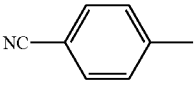 |  | MH⁺ = 506<br>rt = 2.11<br>MS 2 |
| 151 | 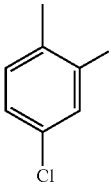 | 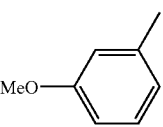 | 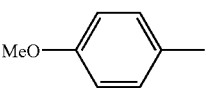 | MH⁺ = 525<br>rt = 2.08<br>MS 2 |
| 152 | 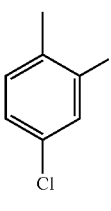 | | | MH⁺ = 526<br>rt = 2.13<br>MS 5 |

TABLE IV-continued

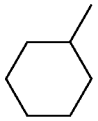

(ID)

| Compound No. | R₂ | R₄ | R₅ | Characterization conditions |
|---|---|---|---|---|
| 153 | 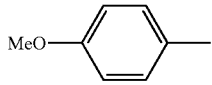 | 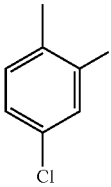 | 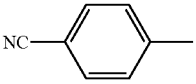 | MH⁺ = 502<br>rt = 2.19<br>MS 5 |
| 154 | 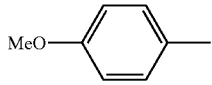 | 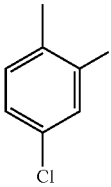 | 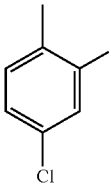 | MH⁺ = 521<br>rt = 2.12<br>MS 5 |

The compounds of formula (I) show very good in vitro affinity ($IC_{50} \leq 5 \times 10^7 M$) for the $CB_1$ cannabinoid receptors, under the experimental conditions described by M. Rinaldi-Carmona et al. (FEBS Letters, 1994, 350, 240-244).

The antagonist nature of the compounds of formula (I) was demonstrated by means of the results obtained in models of inhibition of adenylate cyclase as described in M. Bouaboula et al., J. Biol. Chem. 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as medicaments.

Thus, according to another of its aspects, a subject of the invention is medicaments comprising a compound of formula (I) or an addition salt thereof with a pharmaceutically acceptable acid, or alternatively a solvate or a hydrate of the compound of formula (I).

Thus, the compounds according to the invention may be used in man or animals in the treatment or prevention of diseases involving the $CB_1$ cannabinoid receptors.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention and hyperactivity disorders (AHD) in hyperkinetic children (MBD), and also for the treatment of disorders associated with the use of psychotropic substances, especially in the case of a substance abuse and/or dependency on a substance, including alcohol dependency and nicotine dependency.

The compounds of formula (I) according to the invention may be used as medicaments for treating migraine, stress, diseases of psychosomatic origin, panic attacks, epilepsy, motor disorders, in particular dyskinesia or Parkinson's disease, trembling and dystonia.

The compounds of formula (I) according to the invention may also be used as medicaments in the treatment of memory disorders, cognitive disorders, in particular in the treatment of senile dementia and Alzheimer's disease, and also in the treatment of attention or consciousness disorders. Furthermore, the compounds of formula (I) may be useful as neuroprotective agents, in the treatment of ischemia, cranial trauma and the treatment of neurodegenerative diseases: including chorea, Huntington's chorea and Tourrette's syndrome.

The compounds of formula (I) according to the invention may be used as medicaments in the treatment of pain: neuropathic pain, acute peripheral pain, chronic pain of inflammatory origin.

The compounds of formula (I) according to the invention may be used as medicaments in the treatment of appetite disorders, appetence disorders (for sugars, carbohydrates, drugs, alcohol or any appetizing substance) and/or eating behavioral disorders, especially for the treatment of obesity or bulimia and also for the treatment of type II diabetes or non-insulin-dependent diabetes and for the treatment of dyslipidaemia and metabolic syndrome. Thus, the compounds of formula (I) according to the invention are useful in the treatment of obesity and the risks associated with obesity, especially the cardiovascular risks. Furthermore, the compounds of formula (I) according to the invention may be used as medicaments in the treatment of gastrointestinal disorders, diarrhea disorders, ulcers, vomiting, bladder and urinary disorders, disorders of endocrine origin, cardiovascular disorders, hypotension, haemorrhagic shock, septic shock, chronic cirrhosis of the liver, hepatic steatosis, steatohepatitis, non-alcoholic steatohepatitis, asthma, Raynaud's syndrome, glaucoma, fertility disorders, voluntary interruption of pregnancy, premature interruption of pregnancy, inflammatory phenomena, immune system diseases, in particular autoimmune diseases and neuroinflammatory diseases such as rheumatoid arthritis, reactional arthritis, diseases resulting in demyelinization, multiple sclerosis, infectious and viral diseases such as encephalitis, strokes, and also as medicaments for anticancer chemotherapy, for the treatment of Guillain-Barré syndrome and for the treatment of osteoporosis.

According to the present invention, the compounds of formula (I) are most particularly useful for treating psychotic disorders, in particular schizophrenia, attention and hyperactivity disorders (AHD) in hyperkinetic children (MBD); for treating appetite and obesity disorders; for treating type II diabetes, for treating memory and cognitive deficits; for treating alcohol dependency and nicotine dependency, i.e. for weaning from alcohol and for weaning from tobacco.

More particularly, the compounds of formula (I) according to the present invention are useful for treating and preventing of appetite disorders, metabolic disorders, gastrointestinal disorders, inflammatory phenomena, immune system diseases, psychotic disorders, alcohol dependency and nicotine dependency.

According to one of its aspects, the present invention relates to the use of a compound of formula (I), pharmaceutically acceptable salts thereof and solvates or hydrates thereof for treating the disorders and diseases indicated above.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and also at least one pharmaceutically acceptable excipient.

The pharmaceutical compositions according to the present invention may contain, along with a compound of formula (I), one (or more) other active principle that is useful in the treatment of the disorders and diseases indicated above.

Thus, a subject of the present invention is also pharmaceutical compositions containing a compound of formula (I) according to the present invention combined with one (or more) active principle chosen from one of the following therapeutic classes:

an angiotensin II $AT_1$ receptor antagonist, alone or combined with a diuretic;
a converting enzyme inhibitor, alone or combined with a diuretic or a calcium antagonist;
a calcium antagonist;
a beta-blocker, alone or combined with a diuretic or a calcium antagonist;
an antihyperlipaemiant or an antihypercholesterolaemiant;
an antidiabetic agent;
another anti-obesity agent;
a nicotine agonist or a partial nicotine agonist;
an antidepressant or an antipsychotic agent;
an anticancer agent or an antiproliferative agent;
an opioid antagonist;

and also:
an agent useful in the treatment of alcoholism or weaning symptoms;
an agent useful for treating osteoporosis;
a non-steroidal or steroidal anti-inflammatory agent;
an anti-infectious agent;
an analgesic.

The term "angiotensin II $AT_1$ receptor antagonist" means a compound such as candesartan, cilexitil, eprosartan, irbesartan, losartan potassium, olmesartan medoxomil, telmisartan or valsartan, each of these compounds themselves possibly being combined with a diuretic such as hydrochlorothiazide.

The term "converting enzyme inhibitor" means a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, each of these compounds itself possibly being combined with a diuretic such as hydrochlorothiazide or indapamide or with a calcium antagonist such as amlodipine, diltiazem, felodipine or verapamil.

The term "calcium antagonist" means a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" means a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propanolol, salmeterol, sotalol, talinolol, tertatolol, tilisolol, timolol, xamoterol or xibenolol.

The term "antihyperlipidaemiant or antihypercholesterolaemiant" means a compound chosen from fibrates such as alufibrate, beclobrate, bezafibrate, ciprofibrate, clinofibrate, clofibrate, etofibrate or fenofibrate; statins (HMG-CoA reductase inhibitors) such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterin or tiadenol.

The term "antidiabetic agent" means a compound belonging to one of the following classes: sulfonylureas, biguanidines, alpha-glucosidase inhibitors, thiazolidinediones, metiglinides such as acarbose, acetohexamide, carbutamide, chorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogues. The term "another anti-obesity agent" means a compound such as amfepramone, benfluorex, benzphetamine, indanorex, mazindole, mefenorex, methamphetamine, D-norpseudoephedrine or sibutramine, a lipase inhibitor (orlistat or cetilistat), a PPAR agonist, a dopamine agonist, a leptin receptor agonist, a serotonin receptor inhibitor, a beta-3 agonist, a CCK-A agonist, an NPY inhibitor, an MC4 receptor agonist or a bombesin agonist.

The term "opioid antagonist" means a compound such as naltrexone, naloxone or nalmefene.

The term "agent useful in the treatment of alcoholism and weaning symptoms" means acamprosate, benzodiazepines, beta-blockers, clonidine and carbamazepine.

The term "agent useful for treating osteoporosis" means, for example, bisphosphonates such as etidronate, clodronate, tiludronate or risedronate.

In the pharmaceutical compositions according to the present invention, the excipients are chosen, according to the pharmaceutical form and the desired mode of administration, from the usual excipients known to those skilled in the art.

In the pharmaceutical compositions of the present invention for oral, sublingual subcutaneous, intramuscular, intravenous, topical, local, intratracheal, intranasal, transdermal or rectal administration, the active principle of formula (I)

above, or the possible salt, solvate or hydrate thereof, may be administered in a unit form of administration, as a mixture with standard pharmaceutical excipients, to man and animals for the prophylaxis or treatment of the above disorders or diseases.

The appropriate unit forms of administration include oral-route forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.01 to 100 mg/kg in one or more dosage intakes, preferentially 0.02 to 50 mg/kg.

There may be particular cases in which higher or lower dosages are appropriate; such dosages do not depart from the context of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of formula (I):

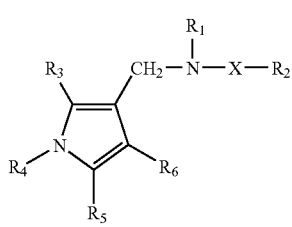

(I)

in which:
X represents a group

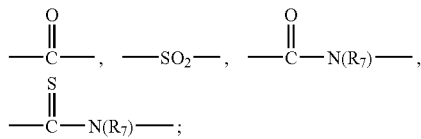

$R_1$ represents a hydrogen atom or a $(C_1-C_3)$alkyl group;
$R_2$ represents:
a $(C_1-C_{12})$alkyl, which is unsubstituted or substituted with one or more substituents independently chosen from a hydroxyl, a $(C_1-C_4)$alkoxy, a trifluoromethyl radical and a trifluoromethoxy radical;
a $(C_3-C_{12})$ non-aromatic carbocyclic radical, which is unsubstituted or substituted one or more times with a $(C_1-C_3)$alkyl or a $(C_1-C_3)$alkoxy;
a $(C_3-C_7)$cycloalkylmethyl, which is unsubstituted or substituted one or more times on the carbocycle with a $(C_1-C_3)$alkyl or a $(C_1-C_3)$alkoxy;
a phenyl, which is unsubstituted or substituted one or more times with substituents independently chosen from a halogen atom, a $(C_1-C_4)$alkyl, a $(C_1-C_4)$alkoxy, a cyano, a trifluoromethyl radical, a trifluoromethoxy radical, a di$(C_1-C_4)$alkylamino radical, a group $S(O)_m$Alk, a $(C_1-C_4)$alkylcarbonyl group, or from a phenyl, 1-pyrrolyl, imidazolyl, pyridyl or pyrazolyl radical, the said radicals being unsubstituted or substituted one or more times with a $(C_1-C_4)$alkyl;
a benzodioxolyl, a dihydrobenzofuryl or a dihydrobenzodioxinyl;
a 1,2,3,4-tetrahydronaplithyl, which is unsubstituted or substituted one or more times with a $(C_1-C_4)$alkyl;
a benzyl, which is unsubstituted or substituted on the phenyl one or more times with substituents independently chosen from a halogen atom, a $(C_1-C_4)$alkyl, a $(C_1-C_4)$alkoxy and a trifluoromethyl or trifluoromethoxy radical, and alpha-unsubstituted or alpha-substituted with a pyrrolyl or phenoxy radical;
a benzhydryl or a benzhydrylmethyl;
a phenethyl, which is unsubstituted or substituted on the phenyl with a halogen, a $(C_1-C_4)$alkyl or a trifluoromethyl radical;
an aromatic heterocyclic radical chosen from thienyl, furyl, pyrrolyl, pyridyl, pyrazolyl, oxazolyl and imidazolyl, said radical being unsubstituted or substituted with one or more substituents independently chosen from a halogen atom, a $(C_1-C_4)$alkyl, a $(C_1-C_4)$alkoxy, a trifluoromethyl radical and a trifluoromethoxy radical;
a methyl substituted with a heterocyclic radical independently chosen from thienyl, furyl, pyrrolyl, pyridyl, pyrazolyl, oxazolyl and imidazolyl, said radical being unsubstituted or substituted with one or more substituents independently chosen from a halogen atom, a $(C_1-C_4)$alkyl, a $(C_1-C_4)$alkoxy and a trifluoromethyl radical;
an indolyl, which is unsubstituted or substituted one or more times with substituents independently chosen from a halogen atom, a $(C_1-C_4)$alkyl, a $(C_1-C_4)$alkoxy, a trifluoromethyl radical, a trifluoromethoxy radical, a group $S(O)_m$Alk, a $(C_1-C_4)$alkylcarbonyl group and a phenyl;
a benzothiazolyl, which is unsubstituted or substituted one or more times with substituents independently chosen from a halogen atom, a $(C_1-C_4)$alkyl, a $(C_1-C_4)$alkoxy, a trifluoromethyl radical, a trifluoromethoxy radical, a group $S(O)_m$Alk, a $(C_1-C_4)$alkylcarbonyl group and a phenyl;

a methyl substituted with one or two $(C_1-C_4)$alkyl and with a phenoxy or 1-pyrrolyl radical, said radical being unsubstituted or substituted with a halogen, a $(C_1-C_4)$alkyl or a trifluoromethyl;

$R_3$ represents a $(C_1-C_5)$alkyl or a $(C_3-C_7)$cycloalkyl;

$R_4$ represents a phenyl, which is unsubstituted or substituted one or more times with substituents independently chosen from a halogen atom, a $(C_1-C_4)$alkyl, a $(C_1-C_4)$alkoxy, a trifluoromethyl radical or a group $S(O)_m$Alk;

$R_5$ represents a phenyl, which is unsubstituted or substituted one or more times with substituents independently chosen from a halogen atom, a $(C_1-C_4)$alkyl, a $(C_1-C_4)$alkoxy, a trifluoromethyl radical or a group $S(O)_m$Alk;

$R_6$ represents a hydrogen atom or a $(C_1-C_5)$alkyl group;

$R_7$ represents a hydrogen atom or a $(C_1-C_3)$alkyl;

m represents 0, 1 or 2; and

Alk represents a $(C_1-C_4)$alkyl.

2. The compound of formula (I) according to claim 1, wherein:

$R_1$ represents a hydrogen atom;

$R_3$ represents a methyl;

$R_4$ and $R_5$ represent as a pair, 2,4-dichlorophenyl and 4-chlorophenyl, 2,4-dichlorophenyl and 4-bromophenyl or 2,4-dichlorophenyl and 4-methoxyphenyl;

$R_6$ represents a hydrogen atom; and $R_7$ represents a hydrogen atom.

3. The compound of formula (I) according to claim 1, wherein:

$R_1$ represents a hydrogen atom;

$R_3$ represents a methyl;

$R_4$ represents a 4-methoxyphenyl, a 4-chlorophenyl, or a 2,4-dichlorophenyl;

$R_5$ represents a 4-chlorophenyl, a 4-methoxyphenyl or a 2,4-dichlorophenyl;

$R_6$ represents a hydrogen atom;

X represents a —CO—, —$SO_2$—, —CONH— or —CSNH— group; and $R_2$ represents a group chosen from a chlorophenyl, a trifluoromethylphenyl, a methoxyphenyl, a cyanophenyl, a 2-phenylphenyl, a trifluoromethylbenzyl, a 4-heptyl, a cycloheptyl, a 3,3,3-trifluoro-2-hydroxy-2-methylpropyl, a 2,2-dimethyl-1-(1H-pyrrol-1-yl)propyl, a 2-indolyl, a 5-methyl-2-trifluoromethyl-3-furyl, a 1-ethyl-3-tert-butyl-5-pyrrolyl, a phenethyl, a 1,2,3,4-tetrahydro-2-naphthyl and 1,2,3,4-tetrahydro-1-naplithyl.

4. The compound according to claim 1, which is chosen from:

N-{[5-(2,4-dichlorophenyl)-1-(4-methoxyphenyl)-2-methyl-1H-pyrrol-3-yl]methyl}-5-methyl-2-(trifluoromethyl)furan-3-sulfonamide;

N-{[1-(4-chlorophenyl)-5-(2,4-dichlorophenyl)-2-methyl-1H-pyrrol-3-yl]methyl}-3-cyanobenzenesulfonamide; and N-{[1-(4-chlorophenyl)-5-(2,4-dichlorophenyl)-2-methyl-1H-pyrrol-3-yl]methyl}-3-methoxybenzenesulfonamide.

5. A process for preparing a compound of formula (I) according to claim 1, comprising:

reacting a compound of formula (II):

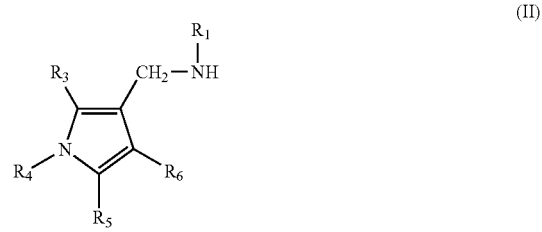

(II)

in which $R_1$, $R_3$, $R_4$, $R_5$ and $R_6$ are as defined for a compound of formula (I) in claim 1, either with an acid of formula (III) or a functional derivative thereof:

HOOC—$R_2$ (III)

in which $R_2$ is as defined in claim 1, when a compound of formula (I) is to be prepared in which —X— represents a —CO— group;

or with a sulfonyl halide of formula (IV):

Hal-$SO_2$—$R_2$ (IV)

in which $R_2$ is as defined in claim 1, and Hal represents a halogen atom, when a compound of formula (I) is to be prepared in which —X— represents an —$SO_2$— group;

or with a haloformate of formula (V):

HalCOOAr (V)

in which Hal represents a halogen atom and Ar represents a phenyl or a 4-nitrophenyl, to obtain an intermediate compound of formula (VI):

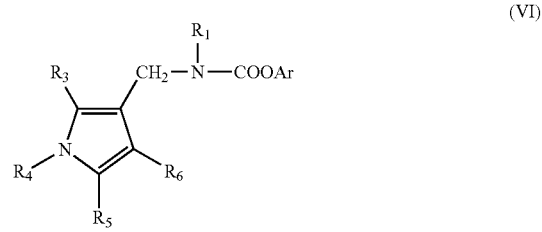

(VI)

in which $R_1$, $R_3$, $R_4$, $R_5$ and $R_6$ are as defined in claim 1; and reacting a compound of formula (VI) with an amine of formula (VII):

HN($R_7$)$R_2$ (VII)

in which $R_2$ and $R_7$ are as defined in claim 1, when a compound of formula (I) is to be prepared in which —X— represents a group —CON($R_7$)—;

or with an isothiocyanate of formula (VIII):

$$R_2\!=\!N\!=\!C\!=\!S \qquad (VIII)$$

in which $R_2$ is as defined in claim 1, when a compound of formula (I) is to be prepared in which —X— represents —CSNH—.

6. A pharmaceutical composition comprising a compound of formula (I) according to claim 1 and at least one pharmaceutically acceptable excipient.

7. A pharmaceutical composition comprising a compound of formula (I) according to claim 2 and at least one pharmaceutically acceptable excipient.

8. A pharmaceutical composition comprising a compound of formula (I) according to claim 3 and at least one pharmaceutically acceptable excipient.

9. A pharmaceutical composition comprising a compound of formula (I) according to claim 4 and at least one pharmaceutically acceptable excipient.

* * * * *